US005623928A

United States Patent [19]
Wright et al.

[11] Patent Number: 5,623,928
[45] Date of Patent: Apr. 29, 1997

[54] METHOD AND APPARATUS FOR COHERENT IMAGE FORMATION

[75] Inventors: J. Nelson Wright, Menlo Park; Samuel H. Maslak, Woodside; David J. Finger, San Jose; Albert Gee, Los Altos, all of Calif.

[73] Assignee: Acuson Corporation, Mountain View, Calif.

[21] Appl. No.: 419,595

[22] Filed: Apr. 7, 1995

Related U.S. Application Data

[63] Continuation of Ser. No. 286,510, Aug. 5, 1994, abandoned.

[51] Int. Cl.[6] .................................................... A61B 8/00
[52] U.S. Cl. ........................ 128/661.01; 73/633
[58] Field of Search .................. 128/660.07, 660.08, 128/661.01; 364/413.25; 367/7, 11, 12, 87, 88; 73/625, 626, 633, 603, 604; 348/95; 359/35, 240, 245

[56] References Cited

U.S. PATENT DOCUMENTS

| 3,805,596 | 4/1974 | Klahr | 73/67.8 |
|---|---|---|---|
| 3,917,380 | 11/1975 | Kato et al. | 359/35 |
| 4,070,643 | 1/1978 | Green | 73/604 |
| 4,140,022 | 2/1979 | Maslak . | |
| 4,191,957 | 3/1980 | Walker et al. | 343/5 PC |
| 4,241,412 | 12/1980 | Swain . | |
| 4,254,662 | 3/1981 | Kuroda et al. . | |
| 4,368,643 | 1/1983 | Tachita et al. . | |
| 4,468,747 | 8/1984 | Leavitt et al. . | |
| 4,471,449 | 9/1984 | Leavitt et al. . | |
| 4,626,907 | 12/1986 | Schedewie | 348/95 |
| 4,733,562 | 3/1988 | Saugeon | 73/626 |

(List continued on next page.)

FOREIGN PATENT DOCUMENTS

| 0473959A2 | 3/1992 | European Pat. Off. . |
|---|---|---|
| 0484181A1 | 5/1992 | European Pat. Off. . |
| 0545788A1 | 11/1992 | European Pat. Off. . |
| 60-80443 | 5/1985 | Japan . |
| 61-228845 | 10/1986 | Japan . |
| 2-193650 | 7/1990 | Japan . |
| 2112937 | 7/1983 | United Kingdom . |
| WO93/12444 | 6/1993 | WIPO . |

OTHER PUBLICATIONS

Casini, et al., "New Envelope Detectors for Biomedical Ultrasound Signals Based on Discrete Coefficient Filters", Digital Signal Processing—84, 1984, pp. 877–881.

Rubin, et al., "Phase Cancellation: A Cause of Acoustical Shadowing at the Edges of Curved Surfaces in B–Mode Ultrasound Images", Ultrasound in Med & Biol., vol. 17, No. 1, 1991, pp. 85–95.

Lamberti et al., "Spurious Echo Generation in Pulse Piezo-electric Transducer For Acoustical Imaging and Its Reduction", Acoustical Imaging, vol. 19, 1992, pp. 219–223.

(List continued on next page.)

Primary Examiner—George Manuel
Attorney, Agent, or Firm—Brinks Hofer Gilson & Lione

[57] ABSTRACT

A method and apparatus are provided for imaging an object using a transducer array for transmitting one or more beams that are steered and/or translated to transmit scan lines for multiple excitation events so as to scan a field of view of the object, for sensing received signals reflected from the object after each excitation event on one or more receive beams on receive scan lines, and for transducing those sensed received signals into corresponding electrical signals. The method and apparatus is additionally for acquiring and storing coherent samples retaining both phase and amplitude information of those electrical signals obtained on the receive scan lines throughout at least a portion of the field of view, and for combining stored coherent samples associated with distinct receive beams to synthesize new coherent image samples aligned on synthetic scan lines which are distinct from any one of (1) receive scan lines on which a signal was sensed, (2) transmit scan lines on which a signal was directed, or (3) transmit scan lines and receive scan lines. The method and apparatus is further for detecting the synthesized coherent image samples and displaying or recording the resulting image field.

139 Claims, 15 Drawing Sheets

U.S. PATENT DOCUMENTS

| | | | |
|---|---|---|---|
| 4,809,184 | 2/1989 | O'Donnell et al. | 364/413.25 |
| 4,817,617 | 4/1989 | Takeuchi et al. | |
| 4,839,652 | 6/1989 | O'Donnell et al. | 341/122 |
| 4,886,069 | 12/1989 | O'Donnell | 128/661.01 |
| 4,983,970 | 1/1991 | O'Donnell et al. | 341/122 |
| 4,989,143 | 1/1991 | O'Donnell et al. | 364/413.25 |
| 5,005,419 | 4/1991 | O'Donnell et al. | 73/626 |
| 5,027,821 | 7/1991 | Hirama et al. | |
| 5,090,795 | 2/1992 | O'Meara et al. | 359/240 |
| 5,105,814 | 4/1992 | Drukarev et al. | 128/660.07 |
| 5,127,409 | 7/1992 | Daigle | |
| 5,128,903 | 7/1992 | Hassler et al. | 367/103 |
| 5,172,343 | 12/1992 | O'Donnell | 128/661.01 |
| 5,197,037 | 3/1993 | Leavitt | 367/11 |
| 5,268,876 | 12/1993 | Rachlin | 128/661.01 |
| 5,278,757 | 1/1994 | Hoctor et al. | 364/413.25 |
| 5,295,118 | 3/1994 | Gilmour | 367/88 |
| 5,318,033 | 6/1994 | Savord | 128/661.01 |
| 5,390,674 | 2/1995 | Robinson et al. | |
| 5,431,167 | 7/1995 | Savord | |
| 5,462,057 | 10/1995 | Hunt et al. | |

OTHER PUBLICATIONS

Mallart et al., "Sound Speed Fluctuations In Medical Ultrasound Imaging Comparison Between Different Correction Algorithms", Acoustical Imaging, vol. 19, 1992, pp. 213–218.

Rahnavard et al., "Phase and Amplitude Reconstruction of an Acoustic Source from the Study of Its Diffraction Pattern", Acoustical Imaging, vol. 19, 1992, pp. 155–159.

Miyashita, Toyokatsu, "Superresolved Image Restoration of Holographic Images by L1–Norm Minimization With Clutter Rejection", Acoustical Imaging, vol. 19, 1992, pp. 77–82.

Timann et al., "Acoustic Self–Imaging in Resiliently Lined Waveguides", Acoustical Imaging, vol. 19, 1992, pp. 149–154.

Kahrs Hansen, Rolf, "Acoustical Imaging Using Spectral Decomposition of the Aperture Field", Acoustical Imaging, vol. 19, 1992, pp. 103–107.

Jones, Hugh W., "Superfesolution in Ultrasonic Imaging", Acoustical Imaging, vol. 19, 1992, pp. 71–76.

Ohno, M., "Acoustic Phase Conjugation Using Nonlinear Electroacoustic Interaction and Its Application To Scanning Acoustic Imaging Systems", Acoustical Imaging, vol. 18, 1991, pp. 65–71.

Hoddinott et al., "Temporal Phase as an Imaging and Correction Tool", Acoustical Imaging, 1988, pp. 303–312.

Nikoonahad, M., "New Techniques in Differential Phase Contrast Scanning Acoustic Microscopy", Acoustic Imaging, 1987, pp. 501–509.

Fink et al., "The Random Phase Transducer: A New Tool for Scattering Medium", Acoustical Imaging, 1987, pp. 445–456.

Johnston, Patrick H., "Sparsely–Sampled Phase–Insensitive Two–Dimensional Arrays: Spatial Interpolation and Signal–Dependent Aperture", Acoustical Imaging, 1987, pp. 19–28.

"Ultrasonic Spectral Analysis for Nondestructive Evaluation", Applications of Ultrasonic Spectroscopy to Materials Evaluation, 1981, pp. 106, 109.

Diagnostic Imaging, May/Jun. 1988.

Robinson, David E., "Digital Reconstruction and Display of Compound Scan Ultrasound Images", IEEE Transactions on Sonics and Ultrasonics, vol. SU–31, No. 4, Jul. 1984, pp. 396–406.

Karaman et al., "VLSI Circuits for Adaptive Digital Beamforming in Ultrasound Imaging", IEEE Transactions on Medical Imaging, vol. 12, No. 4, Dec. 1993, pp. 711–720.

Richard et al., "Real–Time Ultrasounic Scan Conversion Via Linear Interpolation of Oversampled Vectors", Ultrasonic Imaging 16, 1994, pp. 109–123.

Kerr, et al., "Speckle Reduction In Pulse Echo Imaging Using Phase Insensitive and Phase Sensitive Signal Processing Techniques", Ultrasonic Imaging 8, 1986, pp. 11–28.

Ardouin, et al., "Modelling and Restoration of Ultrasonic Phased–Array B–Scan Images", Ultrasonic Imaging 7, 1985, pp. 321–344.

Klingenbeck, et al., "Medical Imaging Techniques", ISPRS Journal of Photogrammetry and Remote Sensing, vol. 45, 1990, pp. 203–226.

Smith, et al., "High–Speed Ultrasound Volumetric Imaging System—Part I: Transducer Design and Beam Steering", IEEE Transactions On Ultrasonics, Ferroelectrics, and Frequency Control, vol. 38, No. 2, Mar. 1991, pp. 100–108.

von Ramm, et al., "High–Speed Ultrasound Volumetric Imaging System—Part II: Parallel Processing and Imaging Display", IEEE Transactions On Ultrasonics, Ferroelectrics, and Frequency Control, vol. 38, No. 2, Mar. 1991, pp. 109–115.

Berkhoff, et al., "Fast Scan Conversion Algorithms For Displaying Ultrasonic Sector Images", Ultrasonic Imaging 16, 1994, pp. 87–108.

Pai–Chai Li, et al., "Blocked Element Compensation in Phased Array Imaging", IEEE Transactions On Ultrasonics, Ferroelectrics, and Frequency Control, vol. 40, No. 4, Jul. 1993, pp. 283–292.

Goldberg, et al., "In Vivo Imaging Using a Copolymer Phased Array", Ultrasonic Imaging 14, 1992, pp. 234–248.

O'Donnell, et al., "Efficient Synthetic Aperture Imaging from a Circular Aperture with Possible Application to Catheter–Based Imaging", IEEE Transactions On Ultrasonics, Ferroelectrics, and Frequency Control, vol. 39, No. 3, May 1992, pp. 366–380.

Lutolf, et al., "Ultrasound Phased–Array Scanner with Digital Echo Synthesis for Doppler Echocardiography", IEEE Transactions On Ultrasonics, Ferroelectrics, and Frequency Control, vol. 36, No. 5, Sep. 1989, pp. 494–506.

Herment, et al., "High–Resolution, Reflection Mode Tomographic Imaging Part I: Principles and Methods", Ultrasonic Imaging 11, 1989, pp. 1–21.

Song, et al., "A New Digital Phased Array System for Dynamic Focusing and Steering with Reduced Sampling Rate", Ultrasonic Imaging 12, 1990, pp. 1–16.

O'Donnell, et al., "Phase Aberration Measurements in Medical Ultrasound: Human Studies", Ultrasonic Imaging 10, 1988, pp. 1–11.

Herment, et al., "High–Resolution, Reflection Mode Tomographic Imaging Part II: Application To Echography", Ultrasonic Imaging 11, 1989, pp. 22–41.

*Beamforming*, Dan E. Dudgeon & Russell M. Mersereau, *Multidimensional Digital Signal Processing*, Section 6.2, Prentice Hall, 1984.

*Digital Time Delay Beamforming*, Roger Pridham, *Signal Processing Handbook*, edited by C.H. Chen, 1988.

*Acoustic Imaging for Nondestructive Evaluation*, Gordon S. Kino, *Proceedings of the IEEE*, vol. 67, pp. 510–525, Apr., 1979.

*Beam Transformation Techniques for Ultrasonic Medical Imaging*, Alex Drukarev, Konstantinoes Konstantinides, Gaidel Seroussi, *IEEE Transactions on Ultrasonics, Ferroelectrics, and Frequency Control*, vol. 40, No. 6, Nov. 1993.

*A Comparison of Algorithms for Polar–to–Cartesian Interpolation in Spotlight Mode Star*, David C. Munson, Jr., Jorge L. C. Sanz, W. Kenneth Jenkins, Gary Kakazu, and Bruce C. Mather, ICASSP, vol. 3, 1985.

*Discrete Fast Algorithms for Two Dimensional Linear Prediction on a Polar Raster*, Wen–Hsien Fang, Andrew E. Yagle, *IEEE Transactions on Signal Processing*, vol. 40, No. 6, Jun. 1992.

*FFT Signal Processing and System Applications*, E. Oran Brigham, Avantek, Inc., *The Fast Fourier Transform and Its Applications*.

*High–Speed Ultrasound Volumetric Imaging System—Part I: Transducer Design and Beam Steering*, Stephen W. Smith, Henry G. Pavy, Jr., and Olaf J. von Ramm, *IEEE Transactions on Ultrasonics, Ferroelectrics, and Frequency Control*, vol. 38, No. 2, Mar. 1991.

*High–Speed Ultrasound Volumetric Imaging System—Part II: Parallel Processing and Image Display*, Stephen W. Smith, Henry G. Pavy, Jr., and Olaf T. von Ramm, *IEEE Transactions on Ultrasonics, Ferroelectrics, and Frequency Control*, vol. 38, No. 2, Mar. 1991.

*Nearest Neighbor and Generalized Inverse Distance Interpolation for Fourier Domain Image Reconstruction*, W. Kenneth Jenkins, Bruce C. Mather, David C. Munson, Jr., ICASSP, vol. 3, 1985.

*The Reconstruction of a Multidimensional Sequence from the Phase or Magnitude of Its Fourier Transform*, Monson H. Hayes, *IEEE Transactions on Acoustics, Speech, and Signal Processing*, vol. 30, No. 2, Apr. 1992.

*Sampling Continuous 2–D Signals*, Dan E. Dudgeon, Russell M. Mersereau, *Multidimensional Digital Signal Processing*, Chapter 1, Section 1.4.

*A Scan Conversion Algorithm for Displaying Ultrasound Images*, Steven C. Leavitt, Barry F. Hunt, Hugh G. Larsen, *Hewlett–Packard Journal*, vol. 34, No. 10, Oct. 1983.

*Support–Limited Extrapolation of Offset Fourier Data*, David C. Munson, Jr. and Eric A. Ullman, *ICASSP*, vol. 4, 1986.

*A Tomographic Formulation of Spotlight–Mode Synthetic Aperture Radar*, David C. Munson, Jr., James Dennis O'Brien, W. Kenneth Jenkins, *Proceedings of the IEEE*, vol. 71, No. 8, Aug. 1983.

Wenmin et al., "The Intelligent Digital Scanning In Phased Array Ultrasonic Tomography", The Journal of the Acoustical Society of America, Supplement 1, vol. 84, Fall 1988, pp. 458–459.

Jiangguo, et al., "A New Digital Processor for Phased–Array Ultrasound System", The Journal of the Acoustical Society of America, Supplement 1, vol. 84, Fall 1988, pp. 456–457.

Umemura et al., "The Sector–Vortex Phased Array: Acoustic Field Synthesis for Hyperthermia", IEEE Transactions in Ultrasonics, Ferroelectrics, and Frequency Control, vol. 36, No. 2, Mar. 1989, pp. 249–257.

Tsukahara et al., "Angular Spectral Approach to Reflection of Focused Beams with Oblique Incidence in Spherical–Planar–Pair Lenses", IEEE Transactions on Ultrasonics, Ferroelectrics, and Frequency Control, vol. 38, No. 5, Sep. 1991, pp. 468–480.

Einighammer, Hans J., "Real–Time Imaging With Area–Array Transducers Using Analog Wave–Field Reproduction and an Application in Transcranial Sonography", Acoustical Imaging, vol. 19, 1992, pp. 421–426.

Weisser et al., "Attenuation Measurement With Transmitted and Reflected Ultrasound—A Comparison of Different Methods", Acoustical Imaging, vol. 19, 1992, pp. 409–414.

Karaman et al., "Optimization of Dynamic Receive Focusing in Ultrasound Imaging", Acoustical Imaging, vol. 19, 1992, pp. 225–229.

Berkhout, A. J., "Ultrasonic Medical Imaging, Current Techniques and Future Developments", Medical Progress Through Technology 11, 1986, pp. 197–207.

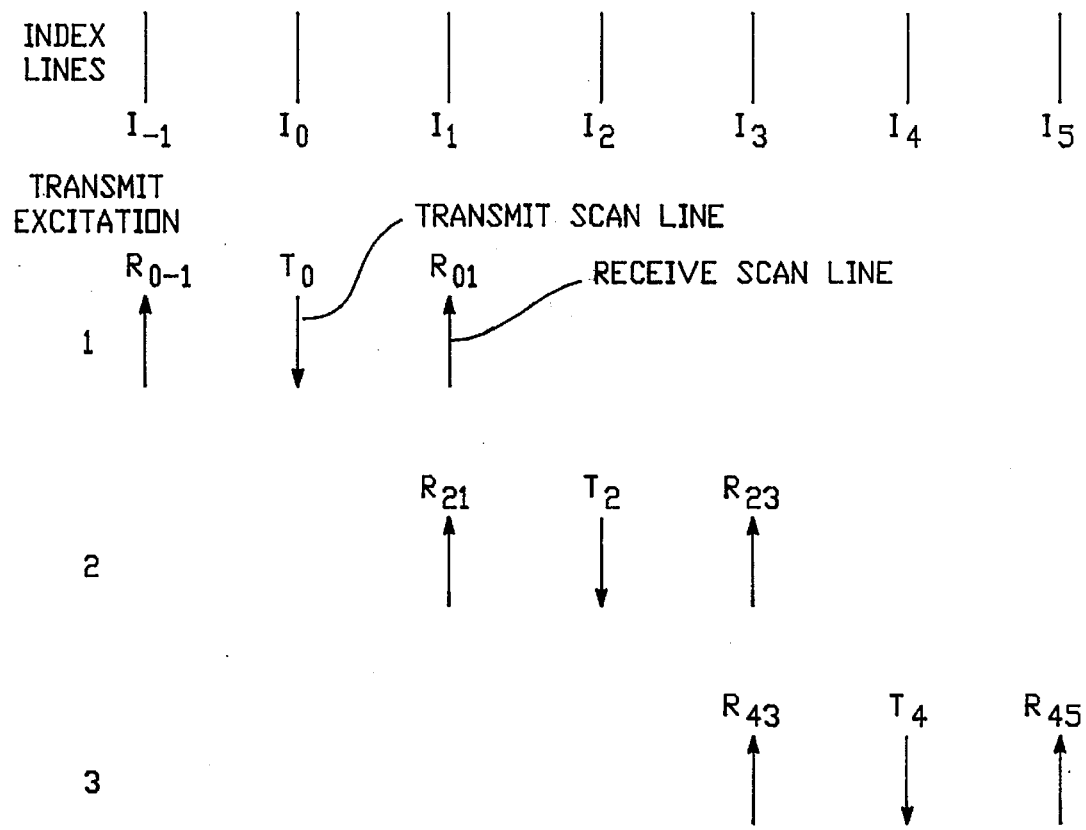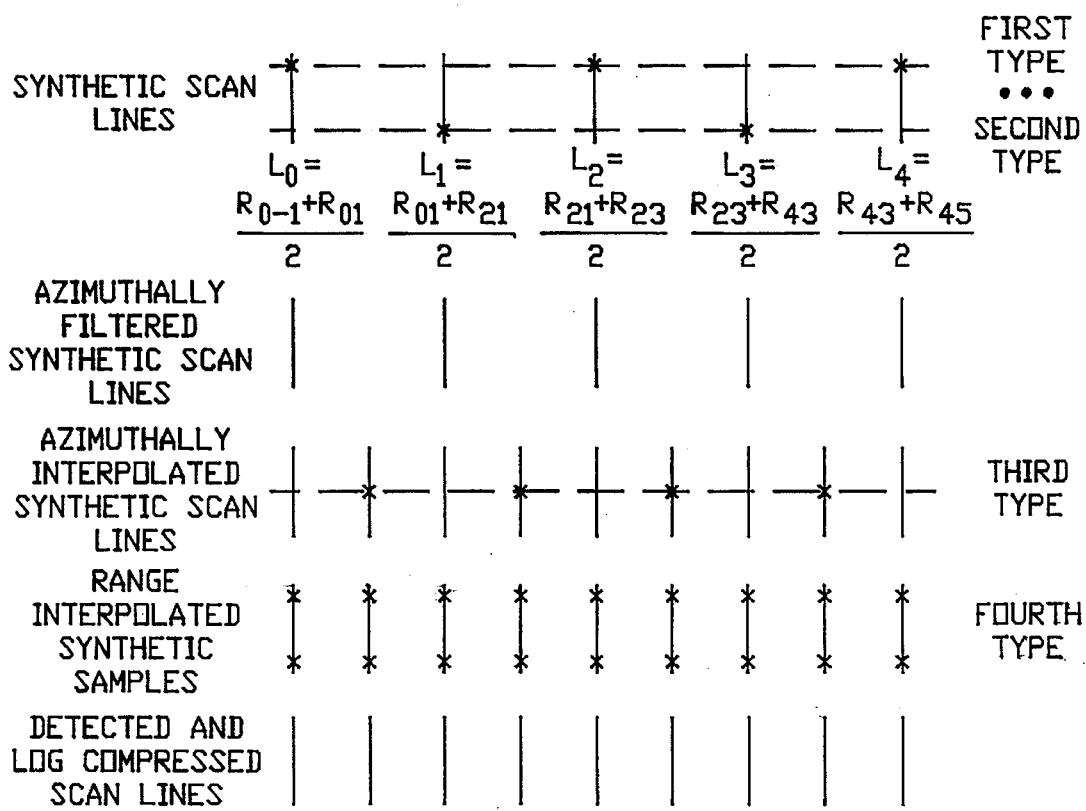
FIG.—1A

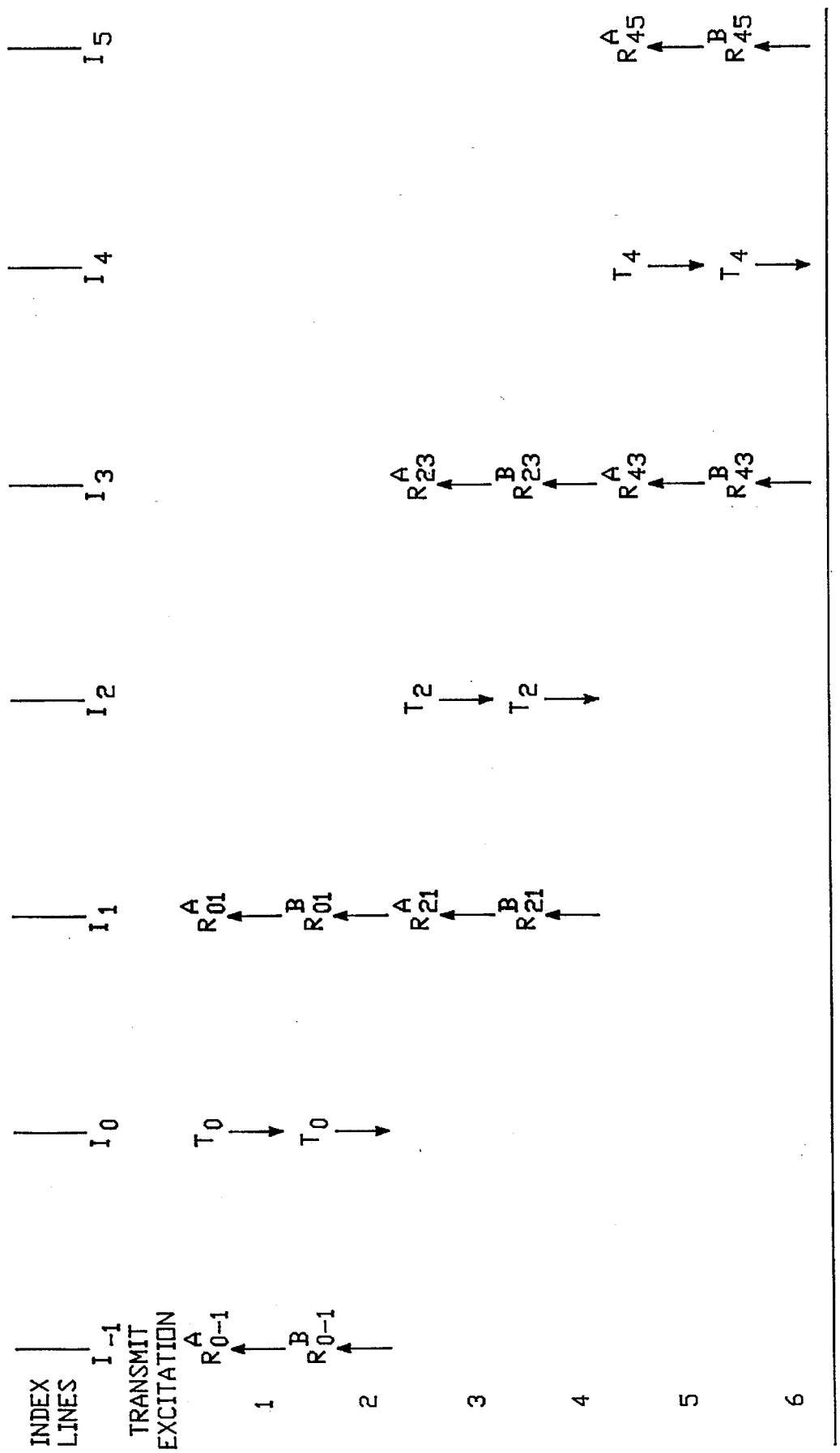
FIG.—1B-1

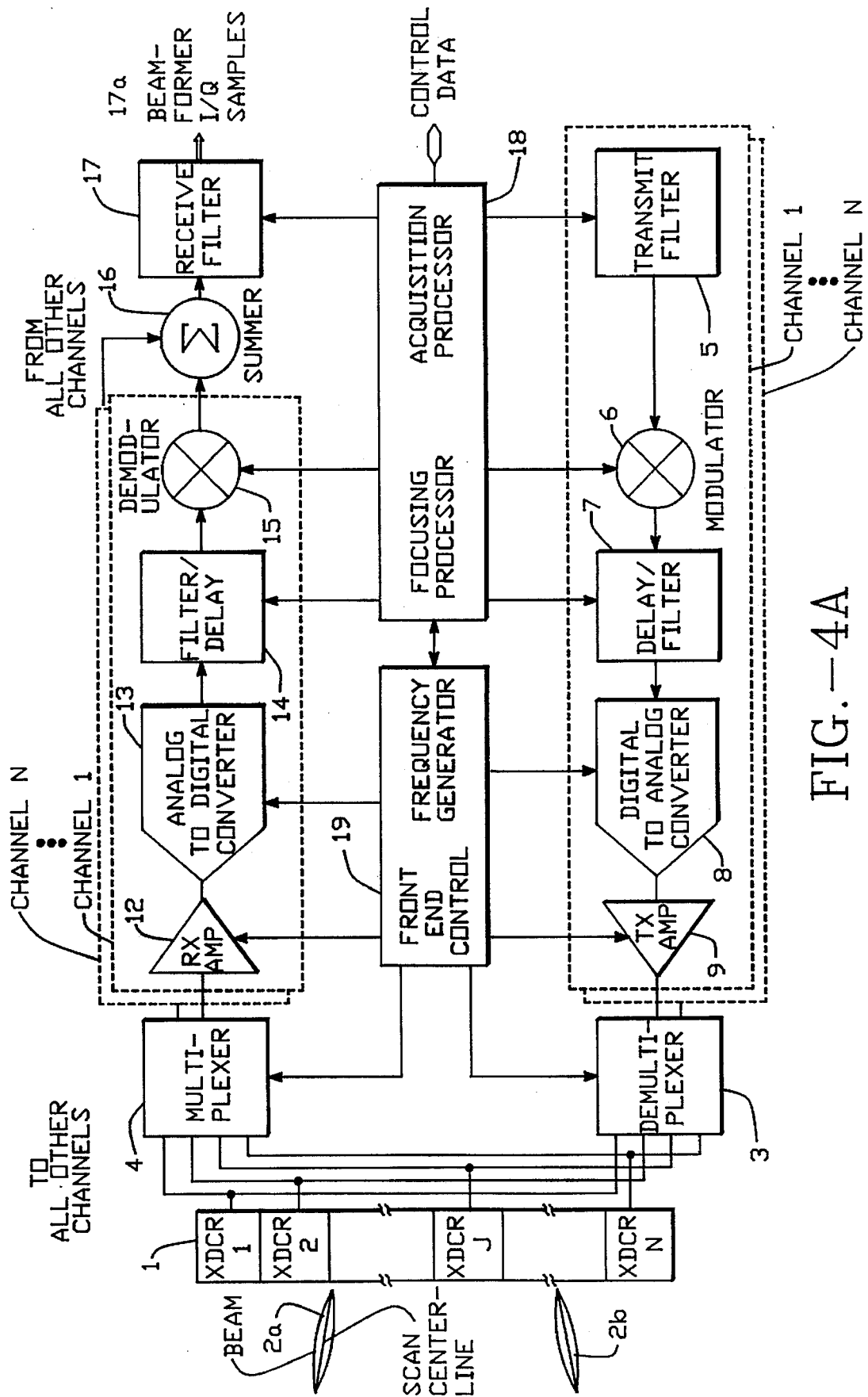
FIG.—4A

GEOMETRY OF SCAN LINES
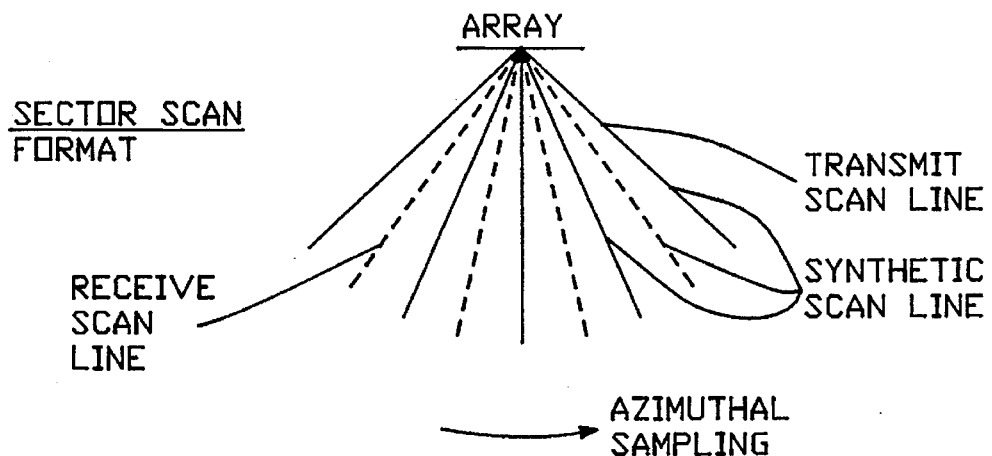
FIG.—6A
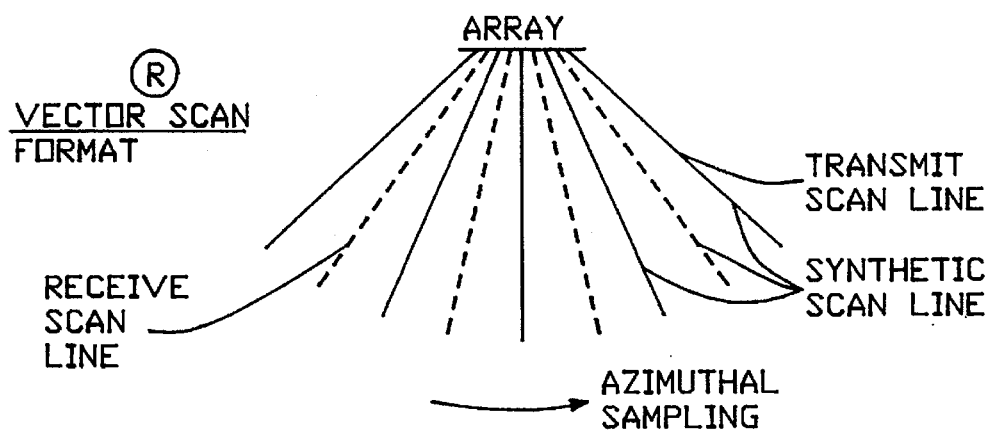
FIG.—6B
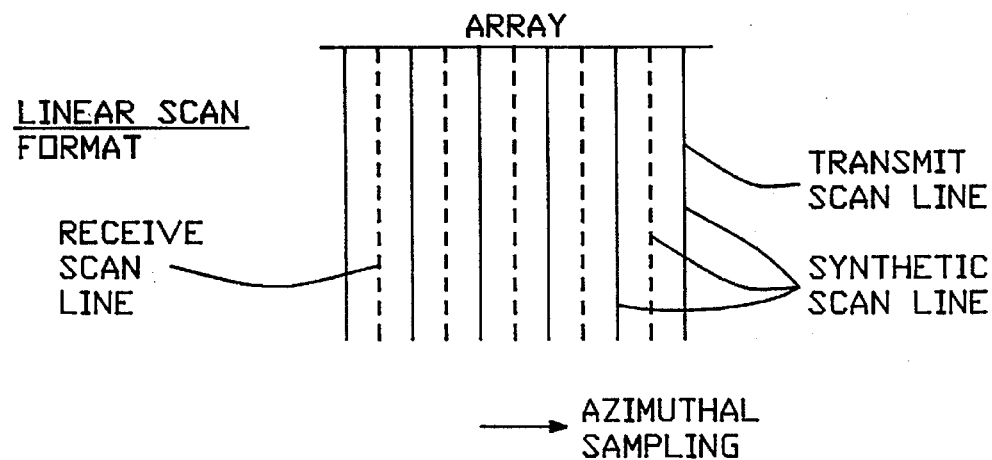
FIG.—6C

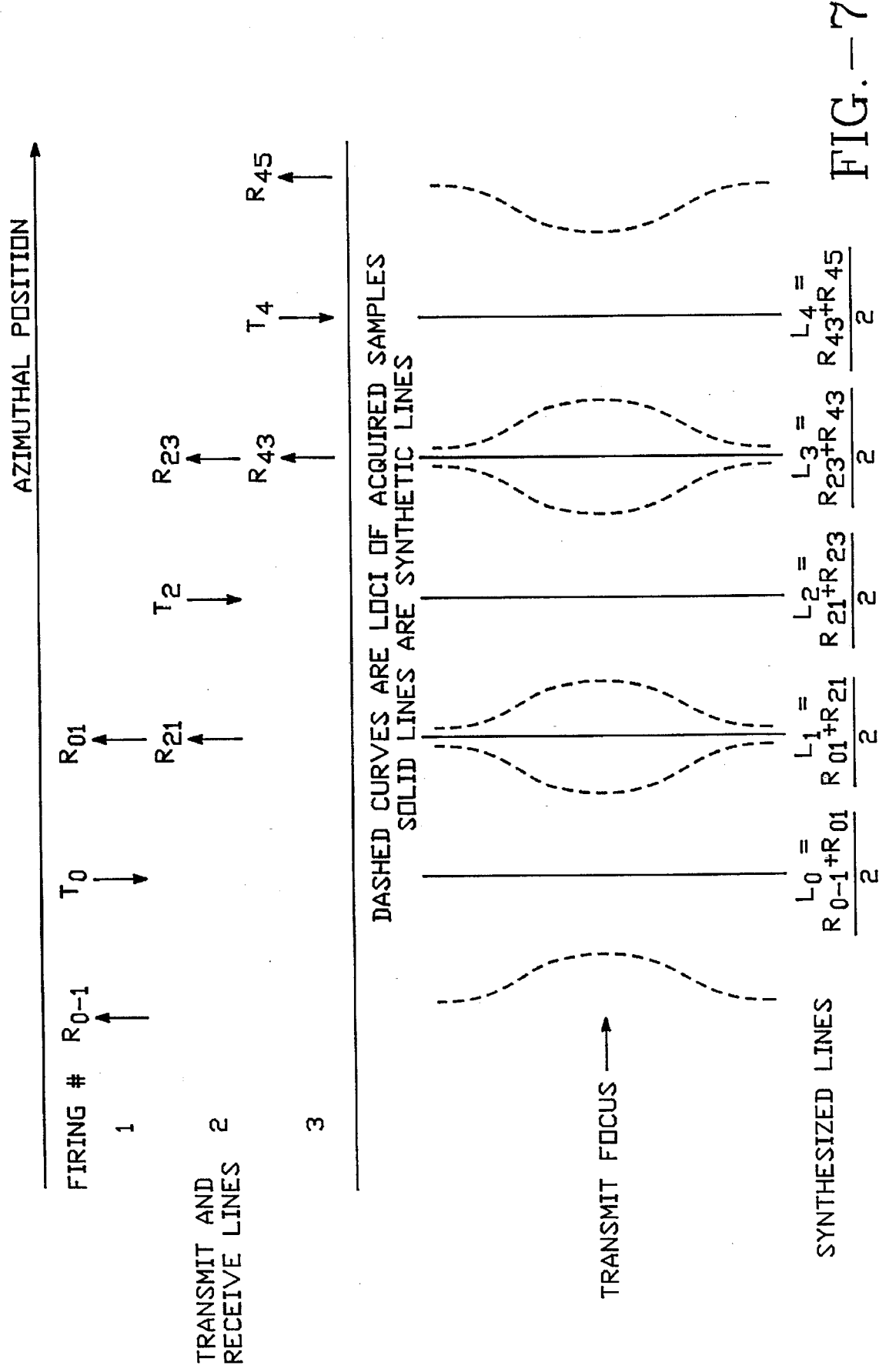

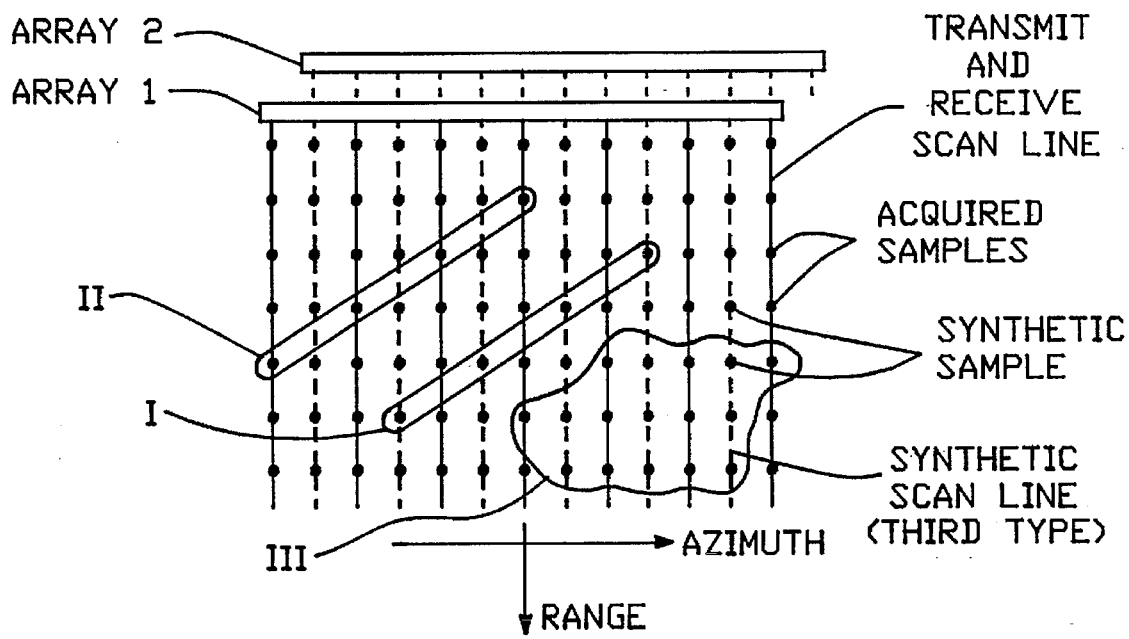
LINEAR SCAN FORMAT
(CARTESIAN COORDINATE SAMPLING)
FIG.—9A
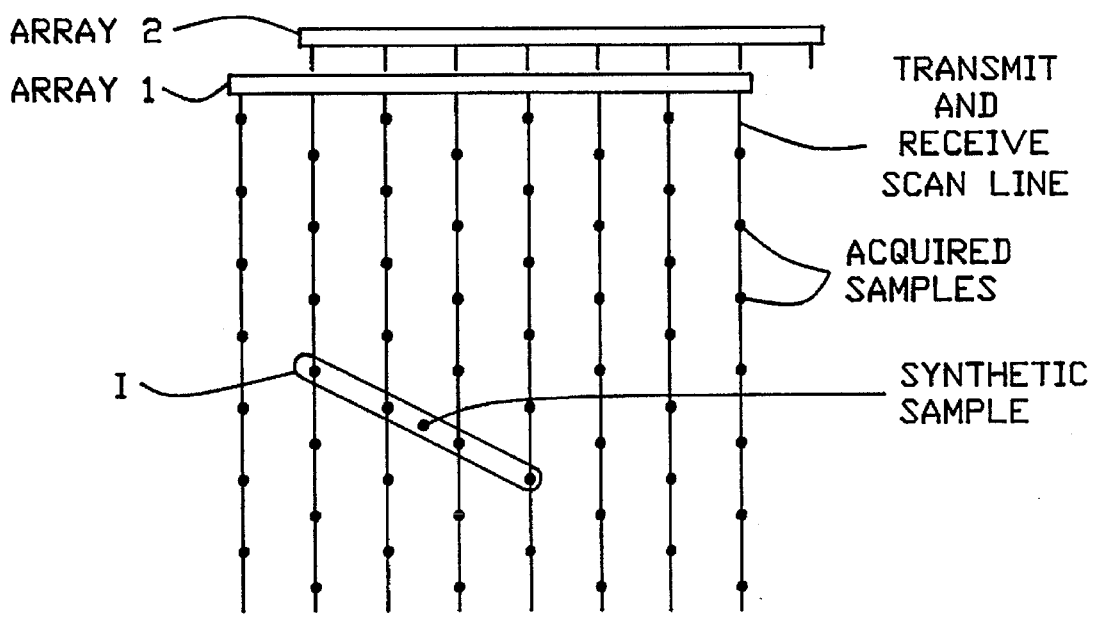
LINEAR SCAN FORMAT
(HEXAGONAL COORDINATE SAMPLING)
FIG.—9B

METHOD AND APPARATUS FOR COHERENT IMAGE FORMATION

This application is a continuation of application Ser. No. 08/286,510, filed Aug. 5, 1994, now abandoned.

CROSS REFERENCE TO RELATED APPLICATIONS

This application is related to the following copending U.S. patent applications:

| Title | Inventors | Atty. Docket No. |
| --- | --- | --- |
| METHOD AND APPARATUS FOR RECEIVE BEAMFORMER SYSTEM | J. Nelson Wright Christopher R. Cole Albert Gee | ACUS-1000 SRM |
| METHOD AND APPARATUS FOR TRANSMIT BEAMFORMER SYSTEM | Christopher R. Cole Albert Gee Thomas Liu | ACUS-1001 SRM/WSW |
| METHOD AND APPARATUS FOR FOCUS CONTROL OF TRANSMIT AND RECEIVE BEAMFORMER SYSTEMS | Albert Gee Christopher R. Cole J. Nelson Wright | ACUS-1002 SRM |
| METHOD AND APPARATUS FOR DOPPLER RECEIVE BEAMFORMER SYSTEM | Samuel H. Maslak Christopher R. Cole Joseph G. Petrofsky | ACUS-1003 SRM/WSW |
| METHOD AND APPARATUS FOR REAL-TIME, CONCURRENT ADAPTIVE FOCUSING IN AN ULTRASOUND BEAMFORMER IMAGING SYSTEM | J. Nelson Wright Samuel H. Maslak Donald R. Langdon Gregory L. Holley Christopher R. Cole | ACUS-1004 SRM/KJD |
| METHOD AND APPARATUS FOR A GEOMETRIC ABERRATION TRANSFORM IN AN ADAPTIVE FOCUSING ULTRASOUND BEAMFORMER SYSTEM | J. Nelson Wright Gregory L. Holley Donald R. Langdon | ACUS-1005 SRM/KJD |

The above related applications are all commonly assigned with the present application, filed concurrently with the present application, and are all incorporated herein by reference in their entirety.

FIELD OF THE INVENTION

This invention relates to coherent imaging systems including, for example, radar, sonar, seismic and ultrasound systems, using vibratory energy, and in particular, but not limited to, phased array ultrasound imaging systems for linear, steered linear, sector, circular, Vector®, steered Vector® and other types of scan formats in, for example, B-mode (gray-scale imaging mode). Although the invention will be discussed with respect to an ultrasound system, the invention can be implemented with other types of coherent imaging systems.

BACKGROUND OF THE INVENTION

There are a number of coherent imaging modalities utilizing electronic beamformation to effect pulse-echo or energy-reflection imaging, in particular radar imaging, ultrasonic imaging and sonar imaging. In many applications, especially real-time medical ultrasonic imaging, it is important to minimize the time necessary to acquire each image (i.e. the time necessary to scan a given field of view) in order to attain a high frame rate.

The requirement to scan a field of view rapidly is always moderated, however, by the need to maintain adequately fine spacing of the beams used to illuminate the field of view and to acquire the image. The spacing of these beams defines an azimuthal sampling grid, referred to as scan lines, and it is well known that the information in the image can be accurately preserved only if this grid is finer than a specific sampling limit in accordance with sampling theorems for one or more dimensions. Prior art systems have often compromised image quality in favor of frame rate by undersampling the field of view. The visible artifact associated with undersampling is shift variance, characterized by sensitivity of the image field to small shifts of the sampling grid with respect to the underlying object field; in an ideal imaging system, the image field has no sensitivity to the positioning of the sampling grid on the object field.

Adequate sampling is made more difficult to achieve by the requirement that the displayed image field consist of detected samples, typically log-magnitude detected samples, although phase detection has also been used in the prior art. Hayes has shown in "The Reconstruction of a Multidimensional Sequence from the Phase or Magnitude of Its Fourier Transform," *IEEE Transactions on Acoustics, Speech and Signal Processing*, Vol. ASSP-30, No. 2, April 1982, pgs. 140–154, that, for cases of interest, an image must be oversampled by a factor of two in each of range and azimuth for all information to be preserved through a process of magnitude detection or phase detection.

The need to scan a field of view rapidly while maintaining adequate line density has been addressed in the prior art with multiple beam techniques, where two or more independent receive beams are simultaneously formed to detect the echoes from one or more simultaneously excited independent transmit beams. An example is O'Donnell U.S. Pat. No. 4,886,069, entitled Method Of And Apparatus For Obtaining A Plurality Of Different Return Energy Imaging Beams Responsive to A Single Excitation Event, issued Dec. 12, 1989, in which multiple receive beams are used in conjunction with one transmit beam. Another multiple beam technique is disclosed in Drukarev, et al., U.S. Pat. No. 5,105,814, entitled Method Of Transforming A Multi-Beam Ultrasonic Image, issued Apr. 21, 1992, in which multiple non-colinear receive beams are formed to align one-for-one with the same multiplicity of transmit beams.

A similar scheme for acquiring three-dimensional images using two-dimensional arrays is disclosed in S. Smith, H. Pavy and O. von Ramm, "High-Speed Ultrasound Volumetric Imaging System-Part I: Transducer Design and Beam Steering" *IEEE Transactions on Ultrasonics, Ferro-Electrics, and Frequency Control*, Vol. 38, No. 2, March 1991, pages 100–108 and in O. von Ramm, S. Smith, and H. Pavy, "High-Speed Ultrasound Volumetric Imaging System-Part II: Parallel Processing and Image Display", *IEEE Transactions on Ultrasonics, Ferro-Electrics, and Frequency Control*, Vol 38, No. 2, March 1991, pages 109–115. For each transmit beam, which illuminates many points, eight simultaneous receive beams are formed.

All of these prior art techniques may reduce the time necessary to scan a field of view, but they can result in a degradation of image quality due to the deliberate misalignment of transmit and receive beams and/or due to interbeam interference when multiple transmit beams are used. The degradation is systematically manifested as shift variance. In the first case, that is because the resulting two-way beams do not generally traverse a straight path (resulting in a position-dependent geometric distortion). In the second case, that is because the resulting two-way beams are not uniform from beam to beam. These artifacts are apparent in systems that utilize focusing for near-field imaging, and they are generally unacceptable in high resolution medical ultrasonic imaging in particular.

SUMMARY OF THE INVENTION

Accordingly the present invention improves upon the prior art.

An object of the present invention is to enable rapid scanning throughout a field of view, and to eliminate or substantially reduce the foregoing artifacts inherent in prior art techniques. Novel aspects of the present invention include (1) use of one or more simultaneously formed receive beams in combination with one or more simultaneously excited transmit beams, (2) storage of coherent samples (i.e., samples that preserve relative amplitude and phase relationships among signals, as defined below) of signals associated with each receive beam, and (3) before detection, synthesis of one or more new coherent samples. The one or more new coherent samples are calculated using stored coherent samples associated with a plurality of distinct receive beams (i.e., two or more receive beams that are associated with spatially different receive scan lines and/or with temporally different transmit excitations, as defined below) through the operations of (a) interpolation (including linear interpolation or weighted sums) or (b) extrapolation or (c) other methods. The one or more new coherent samples are synthesized on synthetic scan lines (i.e., scan lines which are spatially distinct from any receive scan lines and/or any transmit scan lines, as defined below).

A further object of the invention is to increase the sample density after beamformation and prior to detection. Sample density can be increased based on, for example, a two-dimensional data set of acquired samples, and/or a three-dimensional data set of acquired samples.

A further object is the elimination of geometric distortions due to the misalignment of acquired samples with receive scan lines in the prior art.

This invention comprises a method and apparatus capable of the simultaneous transmission of one or more beams of energy on transmit scan lines and of the simultaneous reception of reflected energy with one or more beams on receive scan lines using an electronic beamformer that steers and/or translates both receive and transmit beams independently to effect scanning throughout a given field of view. The system acquires and stores coherent samples of received signals associated with each receive beam and performs interpolations (weighted summations, or otherwise), and/or extrapolations and/or other computations with respect to stored coherent samples associated with distinct receive beams to synthesize new coherent samples on synthetic scan lines that are spatially distinct from the receive scan lines and/or spatially distinct from the transmit scan lines and/or both. The system then in one embodiment detects both acquired and synthetic coherent samples, performs a scan conversion, and displays or records the resulting image field.

Another embodiment of the present invention includes performing scan conversion on acquired and/or synthetic samples prior to detection. Further the act of coherent scan conversion, in and of itself, generates synthetic samples.

In still another embodiment of the present invention, scan conversion of acquired coherent samples is performed prior to the generation of synthetic samples by other techniques of the invention.

In a further embodiment of the invention, scan conversion and the generation of synthetic samples by other techniques of the invention is performed in a merged operation.

An additional feature of the invention is a range-dependent and scan-line-dependent phase shifter or phase aligner. For some scan formats, a phase aligner allows coherent adjustments to be made across the data field of acquired samples to assure proper coherent sample synthesis.

Still another feature of the invention is processing to support synthetic aperture imaging. This processing superposes coherent samples of the received signal associated with temporally distinct transmit excitation events, thus synthesizing larger transmit and/or receive apertures from constituent smaller apertures associated with each event.

A further additional feature of the invention is line-to-line filtering of coherent samples on synthetic scan lines. Such filtering may be used to compensate for periodic gain variations.

Another feature of the invention is azimuthal interpolation and/or extrapolation of coherent samples on distinct receive scan lines and/or on synthetic scan lines.

Still a further feature of the invention is interpolation and/or extrapolation of coherent samples in range along receive scan lines and/or synthetic scan lines. The phase aligning, the synthetic aperture superposition, the filtering, and the interpolation and/or extrapolation in range and azimuth can be incorporated in processing operations separately or in combination.

In both two-dimensional and three-dimensional imaging systems, a feature of the invention is to add synthetic samples at any desired spatial locations and thereby increase the density of the samples in the field.

One embodiment of this invention uses one transmit beam in conjunction with two spatially distinct, non-colinear receive beams, aligned to each side of the transmit beam. This embodiment permits a factor of two decrease in the number of transmit excitation events necessary to adequately scan a given field of view, thus halving the time it takes to scan the field of view. The samples, properly synthesized through combinations of the acquired signals, correspond in quality to receive signals in prior art methods acquired by scanning one line at a time using a single transmit beam aligned with a single receive beam. One principal advantage of this new technique over prior art methods is an increase in frame rate due to the reduction of time necessary to adequately scan the field of view.

Another embodiment of this invention uses one transmit beam ill conjunction with one colinear receive beam. Through interpolation and/or extrapolation, this embodiment permits a factor of two or more increase in the density of scan lines without increasing the time needed to adequately scan a given field of view. This is generally useful for spatial oversampling to improve image quality in many applications, because oversampling is generally necessary to preserve image information through a process of detection.

A preferred embodiment achieves the results of both of the above embodiments, using one transmit beam and two spatially distinct, non-colinear receive beams to effect a factor of two reduction in image acquisition time and a factor of two or more increase in the density of scan lines. This preferred embodiment thus reduces by a factor of four or more the time necessary to acquire image samples on all scan lines, compared to prior art methods in which each scan line is formed with a single transmit beam and a single colinear receive beam. Put another way, the preferred embodiment can acquire and synthesize an oversampled image in half the time that prior art methods can acquire a minimally sampled image in accordance with sampling theorems for two- or three-dimensional systems.

With a spatially stationary target, the technique of this invention is applicable to ultrasound imaging, radar imaging, seismic imaging and sonar imaging. With proper accounting for how a scan is accomplished, the technique of this invention applies to arbitrary sensor array geometry and element spacing. It is extensible to two-dimensional sensor arrays for three-dimensional imaging. It is particularly useful for high resolution systems with relatively large apertures in which prior art multiple beam techniques introduce greater amounts of geometric distortion.

The invention is principally useful for near field, ultrasound medical imaging. It is applicable to all known ultrasound scan formats. It can be advantageously incorporated with dynamic focusing, dynamic apodization, compound transmit focusing techniques, and sequential transmit focusing techniques.

The technique of this invention generates coherent synthetic samples which are compatible with all known types of detection, including magnitude detection, squared magnitude detection, log magnitude detection, phase detection, frequency detection, and arbitrary functions of these detection products. It is compatible with standard techniques for displaying and recording images, including post-detection filtering and persistence, scan conversion, and gray-scale mapping.

BRIEF DESCRIPTION OF THE DRAWINGS

FIG. 1A schematically illustrates a preferred embodiment of this invention for generating synthetic samples on synthetic scan lines.

FIG. 2 schematically illustrates another embodiment of this invention for generating synthetic samples.

FIG. 4A is a schematic block diagram of a digital beamformer that can be used to acquire coherent samples as inputs to embodiments of this invention.

FIGS. 4B-1 and 4B-2 are schematic block diagrams of an embodiment of an apparatus for this invention to effect synthetic samples on synthetic scan lines, with the capability of using synthetic aperture scans.

FIGS. 6A, 15B and 6C are representative of sector, Vector® and linear scan formats which can be used with embodiments of the present invention.

FIG. 7 depicts the preferred embodiment of FIG. 1A with respect to the correction of geometric distortion by generating synthetic samples on synthetic scan lines.

FIG. 9A depicts a linear scan line format where synthetic samples are generated.

FIG. 9B depicts a linear scan line format where hexagonal sampling is employed and where synthetic samples are generated.

DETAILED DESCRIPTION OF THE PREFERRED EMBODIMENT

Figures 1, 1B, 2:
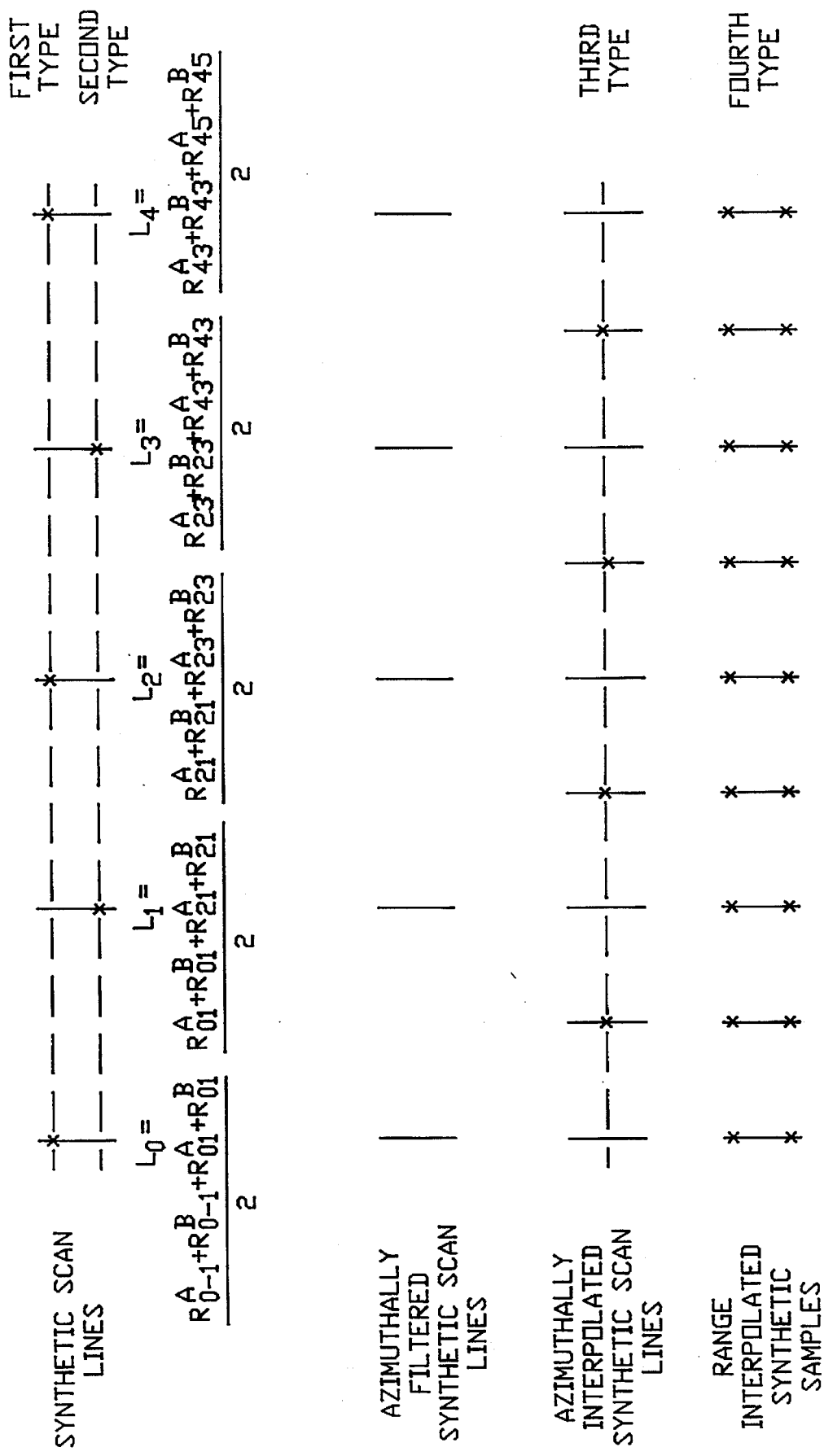
FIGS. 1B-1 and 1B-2 illustrate a preferred embodiment of this invention for generating synthetic samples on synthetic scan lines when synthetic aperture scanning is used.
Figure 2:
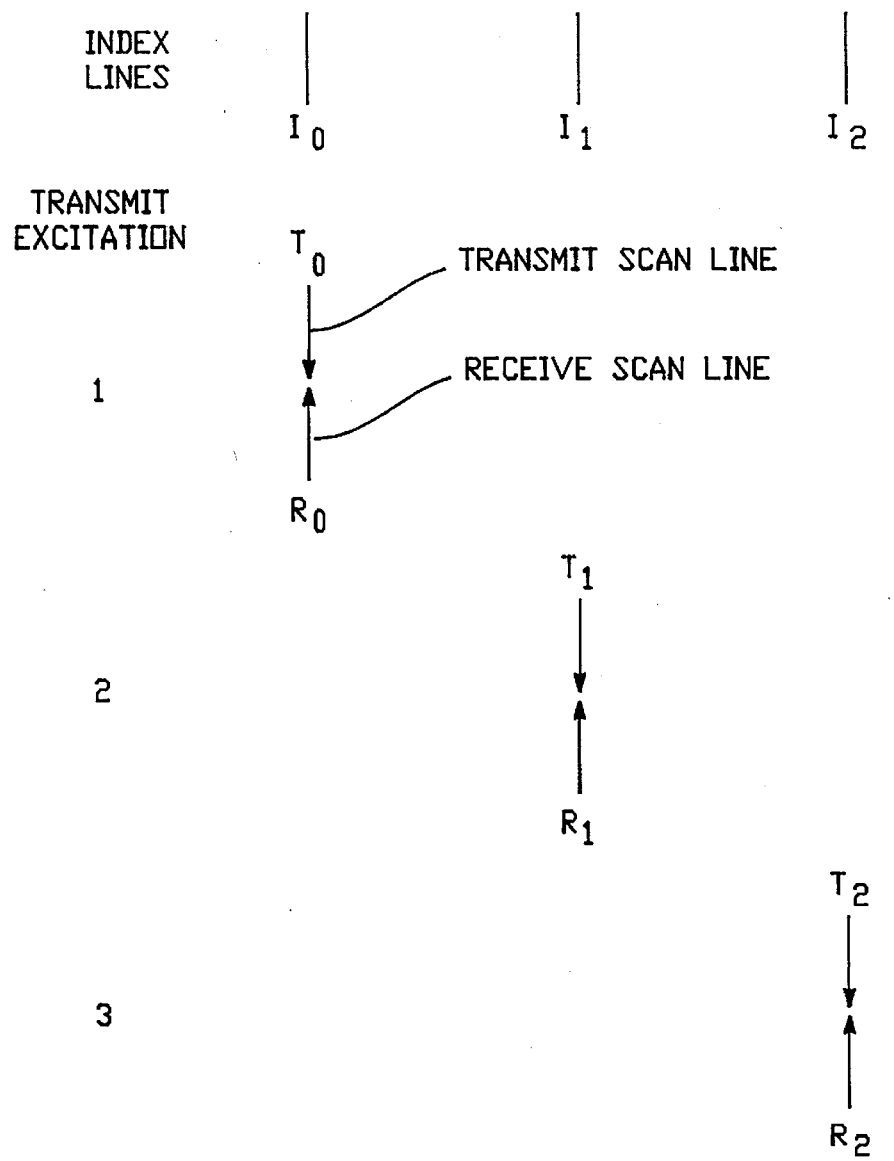

The present invention represents a component of an ultrasound imaging system for which additional patent applications, cross-referenced above, have been simultaneously filed in the United States Patent and Trademark Office. These applications are hereby incorporated by reference.

I. Definitions:

A. Scan Lines:

A scan line is a straight line through space on which samples of an image are presumed to lie. A transmit scan line is such a line on which an associated transmit beam is presumed to lie. A receive scan line is such a line on which an associated receive beam is presumed to lie. In most prior art, transmit scan lines are identical to (i.e., colinear with) receive scan lines.

B. Synthetic Scan Lines:

Synthetic scan lines are scan lines that are distinct from any receive scan lines and/or any transmit scan lines.

Distinct Receive Beams:

Distinct receive beams are receive beams associated with at least one (1) spatially different receive scan lines and (2) temporally different transmit excitations.

D. Synthetic Aperture Scan:

A synthetic aperture scan is a method of acquiring coherent samples on scan lines, effected by partitioning the array of transducer elements into a plurality of independent or substantially independent subarrays for transmission and/or reception, each subarray consisting of multiple transducer elements and executing a plurality of transmit/receive sequences, each sequence involving one transmit excitation and a transmit/receive subarray combination. The transmit and receive beams associated with each sequence in the plurality of sequences are designed to align with the same transmit and receive scan lines, respectively.

E. Coherent Signals and Samples:

The samples of two signals are coherent when sufficient information is stored, preserved, or maintained to enable accurate characterization of the relative amplitude and phase of the complex envelopes of the two signals.

F. Phase Aligned:

Two echo or receive signals are referred to herein as phase aligned if the only difference between their temporal phase variations is due entirely to the interaction of the signals with a target or targets. The process of phase aligning two signals is the process of adjusting the temporal phase variations of one signal or the other, or both, for all systematic distorting influences.

II. Method of Synthesizing Coherent Samples:

A. Samples Synthesized on Synthetic Scan Lines:

This invention comprises a new method for generating coherent samples on synthetic scan lines preferably for medical ultrasonic imaging which enables increased frame rates without the compromises in image quality and resolution inherent in the prior art. The present invention accomplishes this method through increased image sample density with correction for geometric distortion.

The present invention can be used with all known scan formats. Such formats can include by way of example only, sector, Vector® and linear scan formats as depicted in FIGS. 6A, 6B and 6C. Each of these figures depicts an ultrasound transducer, in the form of a phased array, and also indicates transmit scan lines, receive scan lines, and synthetic scan lines in the orientation produced by the method of the preferred embodiment. Further to this point, FIGS. 1A, 1B-1, 1B-2, 2 and 3, described below, show generically the sequencing and relative location of scan lines in the method without reference to any particular scan geometry.

In a preferred embodiment, the method requires sampling, digitization, and storage of signals from multiple receive beams, acquired simultaneously pairwise, each pair associated with a single transmit beam. Such signals must be digitized and stored in coherent form prior to any irreversible processing (such as magnitude detection) which destroys or substantially corrupts signal information. The signals are generally characterized as bandpass processes, and there are a number of well known sampling techniques that will preserve information in such signals. The resulting samples are referred to here as coherent samples, regardless of the details of the sampling technique, because substantially all information about the signal is preserved.

The preferred technique for obtaining coherent samples is through quadrature or complex demodulation of the bandpass signal to baseband, which generates in-phase and quadrature (I and Q) components of the signal. The I and Q components may be regarded as the real and imaginary parts, respectively, of the complex envelope of the bandpass signal. Sampling and digitization may precede or follow the step of demodulation. Means for obtaining the baseband I and Q signals through quadrature demodulation of either analog or digital bandpass signals are well known and common in the signal processing and Doppler processing literature. In particular, the technique is commonly used in medical ultrasound Doppler processing. As discussed below, the invention architecture depicted in FIG. 4A, which is the subject of the above concurrently filed patent applications of the present assignee, can provide the desired coherent samples.

A second and alternative technique for obtaining coherent samples is through direct sampling and digitization of the bandpass signal at a rate that is sufficiently high to preserve information in the signal.

A third and alternative technique is through sampling of an intermediate frequency signal obtained through heterodyning and filtering the original bandpass signal.

The preferred method further requires linearly combining the corresponding coherent samples from distinct receive beams. Non-linear combining techniques are also within the scope of this invention. As indicated previously receive beams are distinct receive beams if they are temporally different (i.e., associated with different transmit events and thus generated non-contemporaneously, even if they align with the same receive scan line) and/or if they are spatially distinct (i.e., aligned with different receive scan lines, even if they are associated with the same transmit event). Such linear combinations may, in the preferred embodiment, be simple averages or other weighted summations of coherent samples associated with two distinct receive beams to form new coherent samples. These new coherent samples lie on synthetic scan lines. Synthetic scan lines are (1) spatially distinct from any receive scan lines (first type, FIG. 1A) or (2) spatially distinct from any transmit scan lines (second type, FIG. 1A) or (3) spatially distinct from both any receive scan lines and any transmit scan lines (third type, FIG. 3 and third type in FIGS. 1A and 1B-2). Other synthetic sample types are discussed below.

The method of this invention further requires beam-to-beam coherent for predictable results from the step of combining coherent samples from distinct receive beams. Beam-to-beam coherency is not required in most prior art ultrasonic imaging systems, although the need for channel-to-channel coherency in phased array imaging systems is well understood. In prior art systems, a requirement for image uniformity is that the amplitude response of the system to a point target at any range on any scan line be substantially identical to the amplitude response to the same target at the same range on an adjacent scan line. The requirement for beam-to-beam coherency in this invention further implies the phase response (jointly represented with the amplitude response by, for example, an in-phase and quadrature response) of the system to a point target at any range on any scan line also to be substantially identical to the phase response to the same target at the same range on an adjacent scan line. Systematic phase variations can arise in some scan formats. For example, if the apertures associated with successive transmit and receive beams change relative to each other, systematic line-to-line phase variations can be introduced. Likewise, systematic line-to-line phase variations can be introduced if the center frequencies of successive transmit and receive beams change relative to each other. This method requires range-dependent and line-dependent phase correction or adjustments of such systematic variations. Such phase corrections or adjustments may be predetermined and stored in memory to be applied by the phase aligner to the acquired coherent samples prior to synthesizing new coherent samples.

As required for this invention and as discussed in co-pending U.S. Patent Application entitled METHOD AND APPARATUS FOR ADJUSTABLE FREQUENCY SCANNING IN ULTRASOUND IMAGING, it is desirable to adjust for systematic phase variations to establish coherent phase alignment among pre-detected beams in a scan. Specifically, it is desirable that the baseband I/Q signal of a first receive beam be phase-aligned at comparable ranges with the baseband I/Q signal of a second receive beam. As previously mentioned, range-dependent phase variations are introduced by certain scan formats which can be systematically corrected by phase rotation prior to detection. Other range-dependent phase variations caused by differences in beam-to-beam transmit/receive frequencies can be systematically corrected by remodulating prior to detection. This is most efficiently performed on the beamformed baseband I/Q signals.

Consider an idealized representation of a signal at the output of a beamformer which has been coherently summed across multiple elements, and has undergone modulation on transmit, demodulation on receive, and coherent summation:

$$x(t-2r/c)=e(t-2r/c) \cdot e^{j[\omega_m \cdot (t-2r/c)]} \cdot e^{-j[\omega_d \cdot t]} \qquad (1)$$

where, $e(t)$=a baseband I/Q signal envelope, $\omega_m=2\pi f_m$=a modulation frequency [Mhz], $\omega_d=2f_d$=a demodulation frequency [Mhz], r=some imaging depth (range) [cm].

Note that the actual center frequency of the imaging pulse, $x(t-2r/c)$, depends additionally on other things, such as tissue attenuation, filtering in the transmit and receive processing chains, and other effects not explicitly considered in the above equation (1). Also not explicitly included in above equation (1) are the detailed representations of delay and phase adjustments necessary for coherent summation, though these could be surmised by those skilled in the art. This detail is not required to motivate the particular results presented here.

The transmit modulation frequency, the receive demodulation frequency, or both, my in general be range dependent. In particular, $$\omega_m = \omega_m(R_t), \text{ and } \omega_d = \omega_d(R_r)$$

where $R_t$=the distance from the active array center to the transmit focus, $R_r$=the distance from the active array center to the receive focus.

For a system with dynamic focus, this means that $\omega_d$ is continuously updated.

We now consider a scan line 1 corresponding to a modulation frequency $\omega_m^1$, a demodulation frequency $\omega_d^1$, and a post-beamformer remodulation frequency $\omega_r^1$; and an adjacent scan line 2, with respective modulation, demodulation, and remodulation frequencies $\omega_m^2$, $\omega_d^2$, $\omega_r^2$. It can be shown that the post-beamformed phase difference between these two scan lines as a result of the different modulation, demodulation and remodulation frequencies can be bounded by an amount $\Delta v$, where $$\Delta v < (\omega_m^2 - \omega_m^1) \cdot T_p - [(\omega_d^2 + \omega_r^2) - (\omega_d^1 + \omega_r^1)] \cdot 2R_r/c \quad (2)$$

where, $T_p$=the imaging pulse duration at any depth of the receive beamformer signal output.

This expression is valid at the receive focal depth, $R_r$, at the point of post-beamformer remodulation. It is again noted that there may be other terms apart from $\Delta v$ which are needed to ensure phase coherence at the beamformer output apart from the above equation (2). Examples of such other terms include, but are not limited to, terms which account for the offset in the beam origin, such as naturally arise in Vector®, linear, and curved linear formats, particularly with end alignment. As expected, $\Delta v=0$ when $\omega_m^2=\omega_m^1$, $\omega_d^2=\omega_d^1$, and $\omega_r^2=\omega_r^1$.

We now make the observation, from the above equation (2), that providing for remodulation at the post-beamformer, pre-detected output with a frequency $\omega_r$ permits scan-line-to-scan-line phase coherence by its proper selection. In particular, by selecting $\omega_r^1$ and $\omega_r^2$ such that $$\omega_d^1 + \omega_r^1 = \omega_d^2 + \omega_r^2 \quad (3)$$

then the second term of equation (2) may be substantially ignored. Note that if $\omega_d$ is range dependent, such as would be the case for a range tracking system, then $\omega_r$ must also be range dependent.

The first term of equation (2), given by $(\omega_m^2 - \omega_m^1) \cdot T_p$ may be readily managed by keeping $(\omega_m^2 - \omega_m^1)$ sufficiently small. As an example, consider the requirement that $\Delta v < \pi/4$, and suppose that, as might be typical, the imaging pulse measured at the point of remodulation for a tracking focused system has a duration that is four cycles of the nominal modulation frequency. Then the required limit on scan-line-to-scan-line frequency variation becomes approximately, from equations (2) and (3), $f_m^2 - f_m^1 < f_m^1/32$. If the nominal modulation frequency is 5 Mhz, then the scan-line-to-scan-line modulation frequency difference is constrained to be less than 0.156 MHz, in this example.

Thus, if post-beamformation, pre-detection receive processing requires beam-to-beam phase coherence for all beams in a scan, then the maximum transmit carrier frequency differential between any two beams in the scan should be chosen to meet the above criteria.

The above relationship (3) defining the remodulation frequencies is independent of the modulation frequencies on transmit. Such independence assumes that both the modulation signal and the demodulation signal for all transmit and receive channels are phase-locked to a common timing clock reference. That is, the phases of all such modulation and demodulation signals are defined relative to a common time reference.

The above relationship (3) also assumes that the modulation frequencies on successive transmit scan lines and the demodulation frequencies on successive receive scan lines are each slowly varying to avoid $2\pi$ phase ambiguities That is, $f_d^1 \approx f_d^2$ and $f_m^1 \approx f_m^2$. This constraint is consistent with the problem being solved.

The above relationship (3) also assumes a "well-focused" system, wherein any observation made concerning a point in the field of view occurs at a time when the receive focus is at that point (i.e. tracking, or dynamic focus), regardless of whether a target is also at that point.

Note that while the above remodulation preferably takes place after receive beamformation and prior to detection, it can instead be performed on a per-channel basis prior to coherent channel summation. Also, note that there may be other systematic phase variations which may need to be corrected in addition to the correction for the varying modulation and demodulation frequencies, such as phase variations introduced by analog filters, transducer elements, and the like. If so, then these corrections should be made as well. Typically, they will merely be added to the phase corrections described above to produce an overall phase correction.

The preferred embodiment of this method is shown schematically in FIG. 1A. For purposes of defining an indexing scheme for scan line intervals, FIG. 1A includes index reference lines $I_1$, $I_1$, $I_2$, $I_3$, $I_4$ and $I_5$. Prior art devices could, for example, have transmit beams sequentially fired on index lines $I_0$ to $I_5$ which would result in transmit scan lines $T_0$, $T_1$, $T_2$, $T_3$, $T_4$ and $T_5$. As can be seen in the embodiment of FIG. 1A, odd transmit scan lines, $T_1$, $T_3$, $T_5$ are missing in accordance with the advantages of the present invention.

The first transmit excitation of FIG. 1A results in a transmit beam aligned with transmit scan line $T_0$. Two receive beans are formed to align with two receive scan lines $R_{0-1}$ and $R_{01}$, positioned preferably symmetrically about $T_0$. It is to be understood that the use of non-symmetrical receive beams is within the spirit and scope of this invention. Similarly, the second temporally distinct transmit excitation results in a transmit beam aligned with transmit scan line $T_2$. Two receive beams are formed to align with two receive scan lines $R_{21}$ and $R_{23}$, positioned preferably symmetrically about $T_2$. In the preferred embodiment, receive scan line $R_{21}$ is colinear with receive scan line $R_{01}$. In other embodiments of this invention, as for example in FIG. 3, such receive scan lines are spatially distinct. This sequence continues until the field of view is sequentially scanned and then the sequence repeats as required. Sequential scanning is preferred rather than random scanning in this embodiment as such scanning more efficiently utilizes the below described apparatus of this invention as sample values are advantageously generated as needed.

Coherent samples of the signals associated with each receive beam are acquired and stored for the subsequent step of synthesizing new coherent samples. The coherent samples on the first synthetic scan line (first type) $L_0$ (which is colinear with transmit scan line $T_0$) are generated by averaging in this embodiment the data associated with receive scan lines $R_{0-1}$ and $R_{01}$. The coherent samples for the second synthetic scan line (second type) $L_1$ (which is colinear with receive scan lines $R_{01}$ and $R_{21}$) are generated by averaging the data associated with receive scan lines $R_{01}$ and $R_{21}$. This sequence continues throughout the field of view. The density of synthetic scan lines at this stage of processing is twice the density of the transmit scan lines.

In practice, for efficiency the first and second types of synthetic samples would be generated in the same embodiment. However, it is to be understood that if desired, only one or the other type of synthetic sample need be generated.

It is to be understood that similar additional synthetic samples, like for example the first type of synthetic samples, can be calculated for multiple other azimuthal positions between $R_{0-1}$ and $R_{01}$ using various types of interpolation techniques as identified herein. Further using extrapolation techniques, synthetic samples can be generated outside of the intervals between $R_{0-1}$ and $R_{01}$.

The method for generating the first and second types of synthetic samples has a principal benefit of correcting for geometric distortion due to the misalignment of acquired samples with receive scan lines. FIG. 7 has many of the same representations as FIG. 1A with the addition of dashed lines to represent the spatial loci of acquired samples and solid lines to represent the previously discussed synthetic scan lines. The geometric distortion would be manifested if acquired samples were presumed to lie on receive scan lines. This presumption and the resulting distortion are inherent in much of the prior art of multiple beam imaging. The averaging step employed by the preferred embodiment of this invention cancels the curvature associated with the acquired samples, and places synthesized samples on synthetic scan lines.

B. Synthetic Aperture Scan:

An alternative scanning technique involves the use of synthetic aperture. Synthetic aperture, in the preferred embodiment of this invention, is characterized by: (1) partitioning the array of transducer elements into a plurality of independent or substantially independent subarrays for transmission and/or reception, each subarray consisting of multiple transducer elements; (2) executing a plurality of transmit/receive sequences, each sequence involving one transmit excitation and a distinct transmit/receive subarray pair, in which each sequence in the plurality of Sequences effects beamformation on the same transmit scan line and the same receive scan lines; (3) for each sequence, acquiring the coherent samples associated with each distinct receive beam; and (4) combining, preferably by summation or weighted summation, all corresponding coherent samples associated with each spatially distinct receive scan line (FIGS. 1B-1 and 1B-2).

Thus, for example, if each sequence involves two transmit excitations, then the method involves summing or otherwise combining coherent data from two temporally distinct receive beams for each receive scan line. The number of transmit and/or receive electronic channels is effectively increased, and the transducer aperture on transmission and/ or reception is increased.

Synthetic aperture scanning is described, for example, in Klahr U.S. Pat. No. 3,805,596, entitled: "High Resolution Ultrasonic Imaging Scanner," and in Saugeon U.S. Pat. No. 4,733,562, entitled: "Method And Apparatus For Ultrasonic Scanning Of An Object." Synthetic aperture scanning is also identified in Kino, "Acoustic Imaging for Nondestructive Evaluation," and Sutton, "Underwater Acoustic Imaging," both in Proceedings of the IEEE, Vol. 67, April 1979. All the above references are incorporated herein by reference.

FIGS. 1B-1 and 1B-2 (with FIG. 1B-1 positioned above FIG. 1B-2 in order to form a diagram of the type depicted in FIG. 1A) illustrates the use of a synthetic aperture method in this invention. The first transmit excitation results in a transmit beam aligned with transmit scan line $T_0$. Two receive beams are formed utilizing a first receive subarray to align with two receive scan lines $R_{0-1}^A$ and $R_{01}^A$ (where the superscript A refers to acquisition after the first transmit excitation), which are positioned, in this embodiment, symmetrically about $T_0$. The second transmit excitation is identical to the first, involving the same transmit aperture and it likewise results in a transmit beam aligned with transmit scan line $T_0$. Two receive beams are formed utilizing a second and different receive subarray, to align with two receive scan lines $R_{0-1}^B$ and $R_{01}^B$ which are colinear with receive scan lines $R_{0-1}^A$ and $R_{01}^A$, respectively (where the superscript B refers to acquisition after the second transmit excitation). Similarly, the third transmit excitation results in a transmit beam aligned with transmit scan line $T_2$, and acquisition proceeds according to FIGS. 1B-1 and 1B-2 on receive scan lines $R_{21}^A$ and $R_{23}^A$ utilizing the first receive subarray. Following that is a fourth transmit excitation and acquisition on receive scan lines $R_{21}^B$ and $R_{23}^B$, again as for the second acquisition using the second and different receive subarray for the fourth acquisition. This sequence continues until the field of view is scanned, and then repeats as required.

Coherent samples of the signals associated with receive scan line $R_{0-1}$ are calculated by summing corresponding samples of $R_{0-1}^A$ and $R_{0-1}^B$, and similarly for receive scan line $R_{01}$ by combining corresponding samples of $R_{01}^A$ and $R_{01}^B$. The coherent samples associated with synthetic scan lines are then generated in the same way as described in connection with FIG. 1A and shown in FIGS. 1B-1 and 1B-2, by this preferred embodiment averaging the data associated with receive scan lines $R_{0-1}$ and $R_{01}$, $R_{01}$ and $R_{21}$, $R_{21}$ and $R_{23}$, $R_{23}$ and $R_{43}$, $R_{43}$ and $R_{45}$, etc. until a complete set of synthesized coherent samples on synthetic scan lines has been combined.

Synthesized coherent samples may be advantageously further processed by, for example, passing equal-range coherent samples through an azimuthal filter. In the preferred embodiment, a three-tap filter with weights of [0.25, 0.5, 0.25] is used, primarily for removal or minimization of line-to-line gain variations. This is also indicated schematically in FIGS. 1A and 1B-2.

Finally, it is noted, as taught above, that synthetic samples can be generated with and/or without using synthetic aperture techniques.

C. Samples Synthesized in Azimuth:

Another embodiment involves the synthesis of additional coherent samples through azimuthal interpolation and/or extrapolation (third type of synthetic sample). This embodiment can be combined with the prior embodiment exploiting the first and second type of synthetic samples as desired. In the preferred embodiment (FIG. 1A), the equal-range I and Q samples associated with each of four adjacent synthetic scan lines are used to interpolate one new sample, also represented in I and Q form, for a new synthetic scan line which is in the middle of the four samples. One of two selectable finite impulse response (FIR) filters is used in the preferred embodiment, the tap weights for one being [0 0.5 0.5 0] and the other being [−0.064 0.564 0.564 −0.064]. This step provides the opportunity to double the azimuthal sample density of the image in order to minimize distortions and artifacts due to subsequent non-linear detection and scan conversion for video display. This third type of synthetic scan line is shown in FIGS. 1A, 1B-1, 1B-2, 2 and 3. As will be apparent to those skilled in the art of linear signal processing, there are many alternative interpolation filters (using different numbers of taps and/or different weights) and many other interpolation factors (to place new synthetic samples at other relative positions) that may be used to advantage. In addition, there are interpolation schemes other than linear interpolation that can be used in order to generate additional azimuthal samples. By way of example only, trigonometric interpolation by Fast Fourier Transform, spline interpolation, and other schemes can be used to increase the azimuthal sample density.

Extrapolation techniques can similarly be used to generate signal samples at, for example, the ends of transducer scans, in order to increase the sample density. By way of example only, a filter arrangement can use four adjacent synthetic samples to generate by extrapolation a fifth synthetic sample positioned azimuthally beyond the span of the four samples.

D. Samples Synthesized in Range:

Another aspect of the preferred embodiment is the synthesis of additional image samples on synthetic scan lines through interpolation and/or extrapolation in range (fourth type of synthetic sample). In the preferred embodiment (FIG. 1A), each four adjacent samples in range on each synthetic scan line are used to interpolate one new coherent sample in the center of the four, also represented in I and Q form. The available interpolation filter tap weights are identical to those of the azimuthal filter. This step doubles the sample density of the image again, this time in range. Range interpolation and/or extrapolation can be carried out using any of the techniques available for azimuthal interpolation and/or extrapolation.

All synthesis operations of the preferred embodiment being complete, each digital coherent sample associated with a synthetic scan line then is converted from its coherent representation to a conventional magnitude detected, log compressed signal, for video raster display or recording. The process of detecting the coherent image samples is the process of converting the samples to the (usually non-coherent) representation of choice for the display or recording device. In alternative embodiments, detection may consist of, or include, phase or frequency detection, or may include a compression curve other than logarithmic, or may include the processing of neighboring coherent samples. The method does not restrict the choice of detection processing.

The subsequent process of displaying or recording the detected samples may typically include spatial filtering (which may be one- or two-dimensional), temporal filtering (i.e., persistence), scan con-version, and gray-scale mapping, after which the signal is sent to the video display device or the recording device. These signal processing elements are commonly used in display and recording subsystems of medical ultrasound imaging systems. The method of this invention Likewise does not restrict the choice of processing steps for displaying or recording the detected signals.

In summary, the described preferred embodiment in FIGS. 1A and 1B includes four types of synthetic samples generated on synthetic lines: the first in which the synthetic samples are formed on a synthetic scan line which is colinear with a transmit scan line, the second in which the synthetic samples are formed on a synthetic scan line which is between two transmit scan lines, the third in which the synthetic samples are formed on a synthetic scan line which is between other synthetic scan lines and not colinear with any transmit or receive scan lines (using azimuthal interpolation), and the fourth where additional synthetic samples are generated in range by interpolation on synthetic scan lines.

E. Alternative Embodiments for Synthesizing Samples in Azimuth and in Range:

The third type of synthetic samples and synthetic scan line can also be generated by an alternative embodiment that relies on conventional (single transmit beam and single receive beam) scanning techniques. This is shown schematically in FIG. 2. The third type of synthetic line can be characterized as an azimuthally (laterally) interpolated synthetic line at a given range, as it is derived through interpolation of conventional (acquired) samples and/or samples generated on other synthetic scan lines (FIG. 1A). In other words, the third type and also the fourth type of synthetic samples can be generated without first generating first type and/or second type synthetic samples. Further with the appropriate hardware, such as for example FIR filters, the first, second and third types of synthetic samples and/or the first, second, third and fourth types of synthetic samples can be generated in one operation. It will also be apparent that another alternative embodiment comprises the calculation of the first two types of synthetic lines, but not the third or fourth type, or alternatively the third or fourth types but not the first or second types.

Further, in summary, all of the above types of synthetic samples, including (1) those that have been processed with an azimuthal filter, (2) those that have been subject to range-dependent and line-dependent phase correction of systematic phase variations, (3) those that have been interpolated in range, and (4) those that have been constructed using a synthetic aperture method, are derived from weighted (real and/or complex weights) summations and/or other interpolations and/or extrapolations and/or other coordination techniques using acquired and/or synthetic coherent samples.

For linear interpolation, weighting and summation may be decomposed several different ways, and into different numbers of distinct steps. For instance, the azimuthal filtering operation in FIG. 1A could occur after, before, or simultaneously with the azimuthal interpolation and/or range interpolation operation. Likewise, the phase correction, as performed by the below described phase aligner, of systematic phase variations could be incorporated in the pairwise combination of receive samples on receive scan lines along with the generation of, for example, first, second or third types of synthetic samples. This implies complex weighting of the I and Q data (where the I and Q signals are treated as the real and imaginary components, respectively, of a complex signal) prior to summation. The specific decomposition of linear signal processing steps in the preferred embodiment of this invention was chosen for efficiency of implementation, and is not a limitation of the method. Further generalizations of the preferred embodiment may also involve weighting and summing coherent samples associated with three or more distinct receive beams in order to synthesize new coherent samples and such weighting and summing operations may be organized and ordered in equivalent ways.

III. Mathematical Treatment of the Preferred Embodiment:

Under conditions that commonly apply in ultrasonic imaging, the process of complex image formation can be modeled as a process of convolution (i.e., filtering) of the object field with the point spread function of the imaging system.

$$i(u)=o(u)*p_{tr}(u) \tag{4}$$

Here, i(u) is the image field, o(u) is the object field, $P_{tr}(u)$ is the point spread function (which is dependent on both the transmit and receive apertures), and * denotes the operation of convolution. A more complete model would include convolution in three dimensions; for simplicity, only the azimuthal (u) response is considered here. It is also well known that, in azimuth, the point spread function $P_{tr}(u)$ can be well approximated as the product of the transmit and receive point spread functions, denoted here $P_t(u)$ and $P_r(u)$, respectively. Thus:

$$p_{tr}(u)=p_t(u) \cdot p_r(u) \tag{5}$$

Consider the first type of synthetic scan line in the preferred embodiment. It is formed by generating a transmit beam on a transmit scan line, then receiving on two receive beams whose receive scan lines are symmetrically located about the transmit scan line, then averaging the signals associated with the two receive beams. We assume for simplicity that the two receive beams are identical except for an azimuthal translation. We may thus associate an effective point spread function with this process:

$$p_{tr_1}(u)=p_t(u) \cdot \tfrac{1}{2}[p_r(u-u_r/2)+p_r(u+u_r/2)] \tag{6}$$

Here, $u_r$ is the spacing of the receive scan lines. Now, consider the second type of synthetic scan line in the preferred embodiment. It is formed by receiving on the same receive beam twice, each time associated with a different transmit event, such that the two transmit scan lines are symmetrically located about the receive scan line. Again, we assume for simplicity that the two transmit beams are identical except for an azimuthal translation. We may likewise associate an effective point spread function with this process:

$$p_{tr_2}(u)=p_r(u) \cdot \tfrac{1}{2}[p_t(u-u_t/2)+p_t(u+u_t/2)] \tag{7}$$

Here, $u_t$ represents the spacing between the transmit scan lines. Finally, consider the third type of synthetic line in the preferred embodiment. It is formed by averaging samples associated with two adjacent round trip scan lines to synthesize new samples associated with another scan line mid-way between the original two. Again, we assume for simplicity that the two round trip beams are identical except for an azimuthal translation. An effective point spread function can be associated with this process:

$$p_{tr_3}(u)=\tfrac{1}{2}[p_{tr}(u-u_{tr}/2)+p_{tr}(u+u_{tr}/2)] \tag{8}$$

Here, $u_{tr}$ represents the spacing between the round trip scan lines.

It is also well known that the azimuthal point spread function is related to the aperture function through a Fourier transform, with proper scaling of the independent variables. Thus equation (5) implies:

$$A_{tr}(x)=A_t(x)*A_r(x) \tag{9}$$

Here, $A_t(x)$ is the transmit aperture, $A_r(x)$ is the receive aperture, $A_{tr}(x)$ is the so-called round trip aperture, and x represents the coordinate position along the aperture.

Consider again the first type of synthetic line. Equation (6) implies:

$$\begin{aligned} A_{tr_1}(x) &= A_t(x) * \tfrac{1}{2}[A_r(x)e^{-j\pi u_r x/\lambda z}+A_r(x)e^{j\pi u_r x/\lambda z}] \\ &= A_t(x)*A_r(x)\cos(\pi u_r x/\lambda z) \end{aligned} \tag{10}$$

Similarly, the second type of synthetic line can be associated with an effective aperture, implied by equation (7):

$$\begin{aligned} A_{tr_2}(x) &= A_r(x) * \tfrac{1}{2}[A_t(x)e^{-j\pi u_t x/\lambda z}+A_t(x)e^{j\pi u_t x/\lambda z}] \\ &= A_r(x)*A_t(x)\cos(\pi u_t x/\lambda z) \end{aligned} \tag{11}$$

Finally, the third type of synthetic line can be associated with an effective round trip aperture, implied by equation (8):

$$\begin{aligned} A_{tr_3}(x) &= \tfrac{1}{2}[A_{tr}(x)e^{-j\pi u_{tr} x/\lambda z}+A_{tr}(x)e^{j\pi u_{tr} x/\lambda z}] \\ &= A_{tr}(x)\cos(\pi u_{tr} x/\lambda z) \end{aligned} \tag{12}$$

Here, $\lambda$ is the wavelength of the carrier frequency and z is the range of interest.

There are two characteristics of importance in equations (10)–(12). First, the synthetic lines thus generated exhibit no steering errors; the aperture associated with the first type of synthetic line has a cosine apodization on the transmit aperture, the aperture associated with the second type of synthetic line has a cosine apodization on the receive aperture, and the aperture associated with the third type of synthetic line has a cosine apodization on the round trip aperture. Second, these cosine apodizations are strictly positive when:

$$u_r < \lambda z/2x$$

$$u_t < \lambda z/2x$$

$$u_{tr} < \lambda z/2x \tag{13}$$

These inequalities apply, of course, to values of x for which the relevant aperture has a non-zero weight. The inequalities are also independent, which means that, for one thing, the transmit and receive apertures need not have the same extent. This implies other strategies for more general embodiments of this invention.

IV. Methods for General Embodiments:

As is well known to those skilled in the art of ultrasonic imaging, the process of filtering described by equation (4) effectively band-limits the image field, due to the finite apertures associated with the point spread functions in equation (5). It follows that there exist spacings of scan lines that permit perfect theoretical reconstruction of the image according to the well known Nyquist sampling criterion. For example, transmit beams produced from an active transmit aperture of finite width $X_t$ focused at range z must be spaced at intervals finer than $z\lambda/X_t$ as a necessary condition for adequate insonification (in a Nyquist sense) of the object field. Here, z is the range from the transducer array along the transmit scan line, and $\lambda$ is the wavelength of the carrier frequency. Likewise, receive beams from an active receive aperture of finite width $X_r$ focused at range z must be spaced at intervals finer than $z\lambda/X_r$ as a necessary condition for adequate sampling of the object field. Finally, if one considers the so-called round trip aperture, given by the convolution of the transmit aperture and the receive aperture, one has a third sampling interval constraint on the spacing of scan lines. They must be spaced at sample intervals finer than $z\lambda/(X_t+X_r)$. All three of these constraints must be met in order to permit lossless insonification and sampling of an object field to preserve all azimuthal information that can be acquired at the range of interest with the apertures and frequency of choice. Equation (13) is an alternative statement of these constraints, in the context of the preferred embodiment of this invention.

There is no required fixed linkage between the transmit and receive scan line spacing, which is useful if the transmit and receive apertures are independently managed. There is also no constraint on how the transmit beams are combined with receive beams. In the preferred embodiment, it is advantageous to combine the transmit beams and receive beams in ways which (1) minimize the previously mentioned geometric distortion, particularly for low f-number imaging in medical ultrasound, (2) minimize the necessary computations and memory requirements, and (3) conveniently exploit the order of data acquisition. However, these choices should not be interpreted as limitations on the generality of the method.

Figure 3:
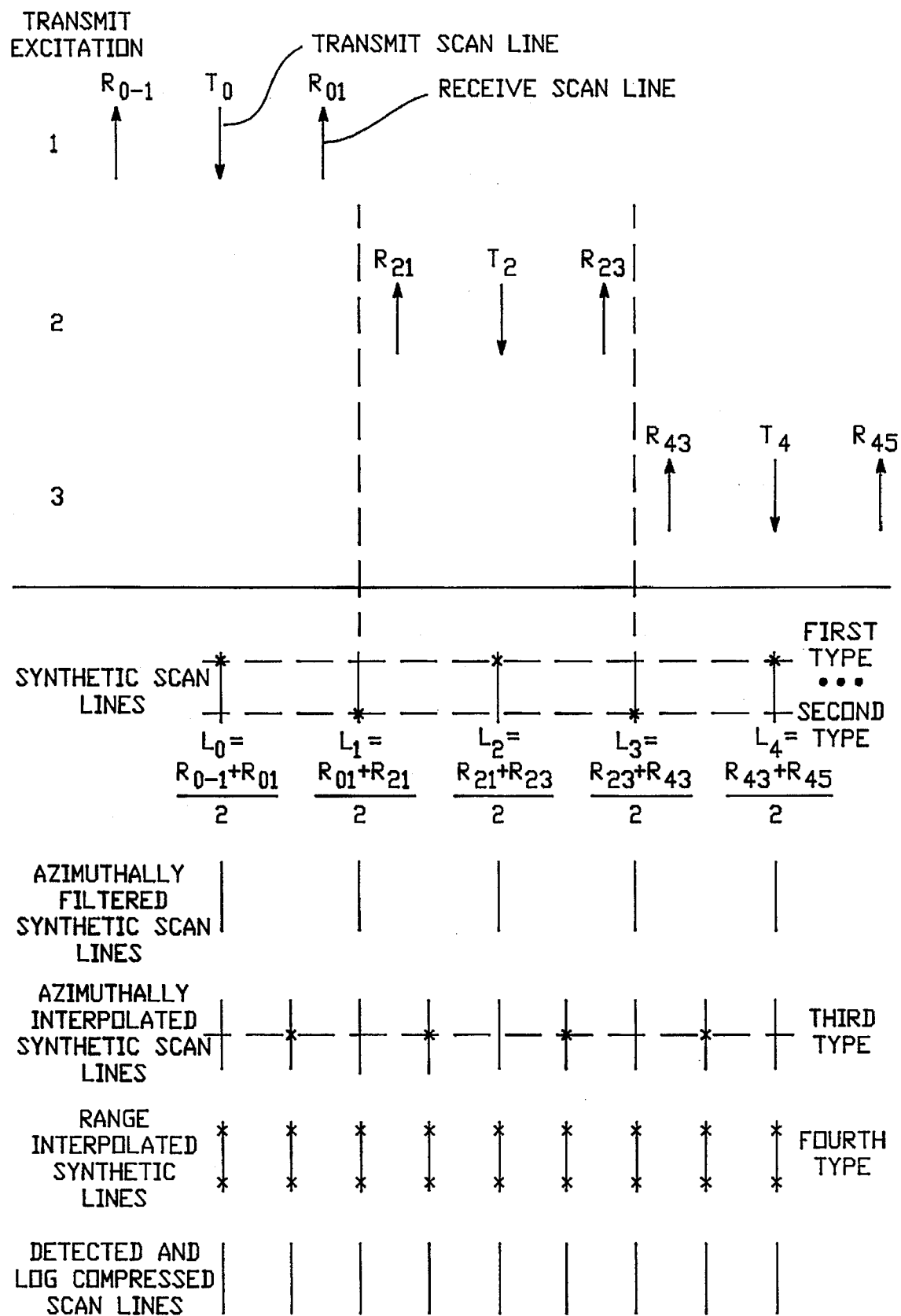
FIG. 3 schematically illustrates still another embodiment of this invention for generating synthetic samples.

A. Methods of Sample Synthesis Using Non-Aligned Receive Scan Lines:

Although FIG. 1A conceptually illustrates a scan scenario in which spacing of receive scan lines about the transmit scan lines $T_0$ and $T_2$ is such that the receive scan lines $R_{01}$ and $R_{21}$ are spatially aligned, this is not required. For example, a configuration such as shown in FIG. 3 is possible. In this example, $R_{01}$ and $R_{21}$ are not spatially aligned, but they can still be advantageously averaged to have a geometric distortion-free scan line midway, in this example, between the receive scan lines at $L_1$, as shown. Such a configuration gives greater latitude in selecting the spacing of acquisition beams. This is an important degree of freedom considering that the receive and transmit apertures are not necessarily linked. However, the resulting spacing of these two synthetic line types is always half of the spacing between adjacent transmit scan lines, independent of the spacing between adjacent receive scan lines. The synthetic scan lines in FIG. 3 also may be acquired with synthetic aperture scanning.

B. Methods of Sample Synthesis Using More than Two Distinct Receive Beams:

Another generalization of the preferred embodiment, which can be applied to either or both of the first and second types of synthetic lines, is the use of samples from more than two distinct receive beams to synthesize new samples on synthetic scan lines. In fact, use of the three-tap azimuthal filter as part of the preferred embodiment indirectly achieves this end because the three weights involve samples on three synthetic scan lines created using samples from six distinct receive beams. A more general approach is motivated by the recognition that synthetic scan lines can be interpolated with arbitrary accuracy by using more and more distinct receive beams that are spaced at Nyquist intervals, such as those given by equation (13).

C. Method of Sample Synthesis Using Multiple Simultaneous Transmit/Receive Beams:

Still another generalization of the preferred embodiment is the use of more than one simultaneously excited transmit beam, and/or more than two simultaneously acquired receive beams. The synthetic line scanning of this invention is the weighted coherent summation, and/or other combinations as discussed above, of distinct receive beams, each associated with one or more transmit beams to form a multiplicity of distinct transmit-receive pairs. This may be generalized for the use of weighted coherent summation, based on equation (9), as follows:

$$A_{tr}(x) = \sum_{n=0}^{N-1} a_n[A_{t_n}(x)e^{j2\pi k_n x} * A_{r_n}(x)e^{j2\pi i_n x}] \quad (14)$$

In equation (14), there are N distinct transmit-receive pairs involved in the generation of the synthetic scan line that can be associated with the conceptual aperture $A_{tr}(x)$. There are likewise N weighting coefficients $a_n$, but there can only be as many distinct coefficients as there are distinct receive beams in the summation. Equation (14) also generalizes the preferred embodiment by incorporating distinct transmit and receive apodizations associated with the lines that are summed. The transmit and receive phase slopes, $k_n$ and $i_n$, account for phase shift due to the spacing of the transmit and receive scan lines. While sampling theorems such as Nyquist's dictate a necessary minimum sampling interval for lossless sampling of the object field, it is not necessary to achieve this sampling density in order to create synthetic lines. There may be conditions under which some degree of undersampling is tolerable, in particular when it results in faster scanning throughout the field of view.

The first, second and third types of synthetic scan lines incorporated in the preferred embodiment are special cases of equation (14), including those synthetic scan lines involving phase correction, synthetic aperture scanning, and azimuthal filtering. Also equation (14) suggests a simple interpretation of the underlying principle involved with synthesizing scan lines: each synthesized coherent sample can be associated with an aperture that is a weighted superposition of the convolved transmit and receive apertures involved with acquiring its constituent samples.

D. Methods of Sample Synthesis Using Neighborhood Interpolation, Hexagonal Sampling and Other Techniques:

The above-described methods rely on one-dimensional (azimuth or range, taken independently) processing and analytical techniques. There are extensions to these techniques which utilize two- or three-dimensional processing and analytical techniques, which processing and analytical techniques are known to those skilled in the art. Such techniques are taught in, for example, "Multidimensional Signal Processing", Dudgeon and Mersereau, Prentice-Hall, 1984. They include hexagonal sampling, as described below, and two- and three-dimensional interpolation and extrapolation techniques by which, for example, the first, second, and third types of synthetic samples can be generated with acquired samples located at unequal ranges. Such techniques also permit new types of synthetic samples to be generated, in particular synthetic samples in elevation for three-dimensional imaging.

One alternate embodiment of this method for two- and three-dimensional imaging involves increasing the sample density through the generation of samples that are located neither in range nor along an azimuthal direction, but at some angle to both of these directions. Thus, using the field of data, additional samples can be synthesized using any of the above interpolation and/or extrapolation techniques along directions other than the range or azimuthal direction as shown for the linear scan format in FIG. 9A. Example I in FIG. 9A, selects four synthetic samples that are aligned at an angle to both the range and azimuth directions. These four samples can be combined using interpolation techniques to generate a new synthetic sample. Example II is similar to Example I except four acquired samples: are used to interpolate a synthetic sample between the four. Example III is similar to the above but uses a neighborhood of acquired and/or synthetic samples from which to generate an additional synthetic sample by, for example, interpolation.

The neighborhood is a space that has dimensions both in range and azimuth for a two-dimensional image and in range, azimuth and elevation (perpendicular to both range and azimuth) for a three-dimensional image.

In Example III, synthetic samples can be generated using (1) only acquired samples, (2) only other synthetic samples or (3) both acquired and other synthetic samples which are located in the neighborhood, and the neighborhood can be located in two or three dimensions. A three-dimensional neighborhood could be created using, for example, two parallel arrays as shown in FIG. 9A to capture samples in the planes of both Array 1 and Array 2.

Another embodiment of this method for increasing the sample density is through the use of hexagonal sampling. A two-dimensional hexagonal sampling method could be used, for example, with the embodiment of FIG. 2 as further depicted in FIG. 9B. Using hexagonal sampling, the target can be scanned about 14% faster, as the spacing between receive scan lines is about 14% greater. With interpolation and/or extrapolation techniques, synthetic samples can be generated using the acquired samples collected by the hexagonal scanning technique (Example I, FIG. 9B) with resulting acquired and synthetic sample densities similar to the non-hexagonal techniques used in FIG. 9A but obtained at a faster rate.

Yet another embodiment of this method involves scanning a three-dimensional image using a two-dimensional array. Just as the use of the first and second types of synthetic samples can halve the time necessary to scan the field of view for a two-dimensional image, so can the use of similar processing quarter the time necessary to scan the field of view for a three-dimensional image. In this embodiment, the density of transmit scan lines is reduced by a factor of two in each of azimuth and elevation, on a rectangular grid, and each transmit excitation is followed by the reception of data on, for example, eight receive beams. These eight receive beams align with eight receive scan lines, also on a rectangular grid, oriented symmetrically about each transmit scan line. Coherent samples on synthetic scan lines are generated by combining samples from distinct receive beams, similar to the two-dimensional case. Transmit scan lines may also be oriented for hexagonal sampling (rather than on a rectangular grid), which permits greater scan line spacing, resulting in even less time necessary to scan the field of view. Other extensions of the methods to three-dimensional scanning, including the incorporation of synthetic aperture scanning and the use of multiple transmit beams, will be understood by those skilled in the art.

Figure 8A:
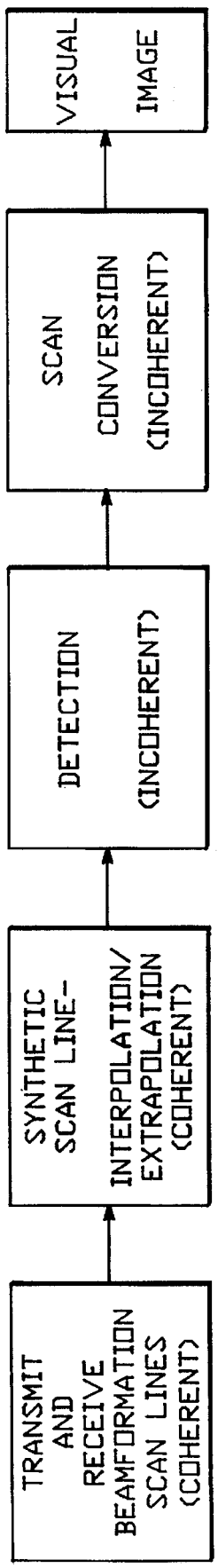
FIGS. 8A, 8B and 8C schematically represent three embodiments of the present invention, with FIG. 8A illustrating the embodiment depicted in FIGS. 4B-1 and 4B-2.

E. Methods of Sample Synthesis Using Scan Conversion Techniques:

The sequential processing of the preferred embodiment is depicted in FIG. 8A. That embodiment sequentially includes first acquiring coherent samples of the ultrasound signals on one or more receive beams along receive scan lines. Once this is accomplished, then synthetic samples on synthetic scan lines can be generated using the above techniques. This includes the generation of the first, second, third and fourth types of synthetic samples. These samples are all coherent. Following the generation of synthetic samples, the synthetic samples, and if desired the acquired samples, are detected by an incoherent process. Following detection, the samples are scan converted in order to put the data in appropriate format for a video display. Finally, the data is represented in a visual image. Scan conversion is a known technique involved in changing the data from a first coordinate system which is, for example, that associated with the sector scan format (FIG. 6A) to a second coordinate system such as that associated with a raster video display. By way of example only, the following article and patents, which are incorporated herein by reference, disclose methods of accomplishing scan conversion: Steven C. Leavitt, Bary F. Hunt, Hugh G. Larsen, "Scan Conversion Algorithm for Displaying Ultrasound Images," *Hewlett-Packard Journal*, October 1983, Vol. 34, No. 10, pgs. 30–34, U.S. Pat. No. 4,191,957 entitled: "Method of Processing Radar Data From a Rotating Scene Using a Polar Recording Format," and issued on Mar. 4, 1980, listing Jack L. Walker and Walter G. Carrara as inventors, and U.S. Pat. No. 5,318,033 entitled "Method and Apparatus For Increasing The Frame Rate And Resolution Of A Phased Array Imaging System," and issued on Jun. 7, 1994, listing Bernard J. Savord as inventor.

Figure 8B:
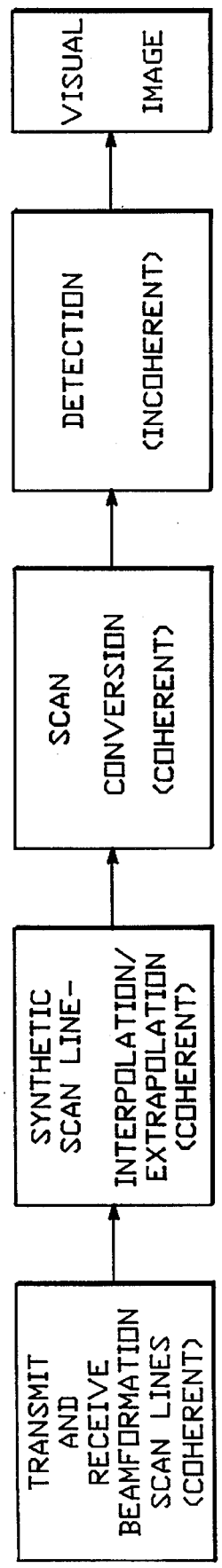

FIG. 8B depicts an alternative embodiment for creating synthetic samples. In FIG. 8B, after coherent samples are generated on synthetic scan lines, the synthetic samples, and if desired the acquired samples, are then scan converted in a coherent manner prior to detection. After scan conversion, the samples are detected in a incoherent operation through the detection step and then displayed.

Figure 8C:
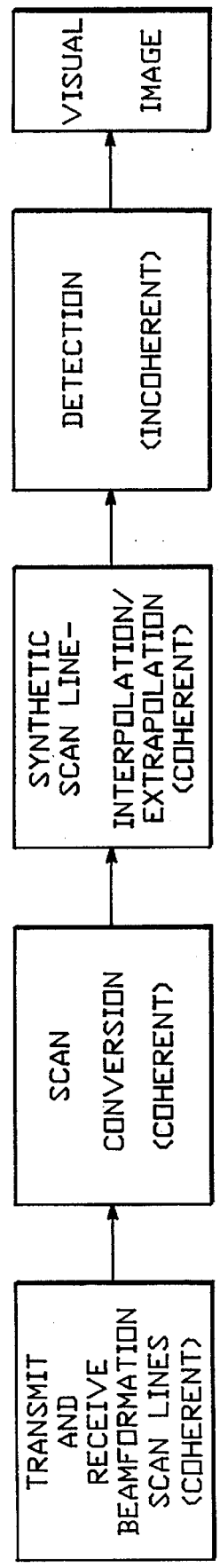

In yet another embodiment of the present invention as shown in FIG. 8C, the acquired samples are scan converted in a coherent manner. Thereafter, scan converted synthetic samples are generated in accordance with the various types of synthetic sampling techniques. The synthetic samples, and if desired, the original scan converted samples, are then detected incoherently and visually displayed. It is to be understood that with respect to the embodiments of FIG. 8B and 8C that the scan conversion and synthetic sample generation can occur in a simultaneous operation. Thus, for example, through the process of scan conversion, not only can samples be moved from one coordinate system to another, but additional samples can be generated during the conversion in order to increase the sample density.

V. Apparatus for Synthesizing Coherent Samples:

FIG. 4A is an example of one of a number of ultrasound beamformer systems that can be used with the present invention. This system is described below and is also described in the above identified and copending patent applications which are assigned to the present assignee and incorporated herein by reference. FIG. 4A is a block diagram of the beamforming elements of a phased array imaging system. An example of an alternative beamformer system is the above O'Donnell U.S. Pat. No. 4,886,069, which uses baseband processing of the digital signals. By way of example only additional beamformers, which could be used with the invention, include the systems which are described in the following U.S. Patents which are incorporated herein by reference in their entirety:

| U.S. Pat. No.: | Title: | Inventor(s): |
| --- | --- | --- |
| 4,809,184 | METHOD AND APPARATUS FOR FULLY DIGITAL BEAM FORMATION IN A PHASED ARRAY COHERENT IMAGING SYSTEM | Matthew O'Donnell<br>Mark Magrane |
| 4,839,652 | METHOD AND APPARATUS FOR HIGH SPEED DIGITAL PHASED ARRAY COHERENT IMAGING SYSTEM | Matthew O'Donnell<br>William E. Engeler<br>Thomas L. Vogelsong<br>Steven G. Karr<br>Sharbel E. Noujaim |
| 4,983,970 | METHOD AND APPARATUS FOR DIGITAL PHASED ARRAY IMAGING | Matthew O'Donnell<br>William E. Engeler<br>John J. Bloomer<br>John t. Pedicone |
| 5,005,419 | METHOD AND APPARATUS FOR COHERENT IMAGING SYSTEM | Matthew O'Donnell<br>Kenneth B. Welles, II<br>Carl R. Crawford<br>Norbert J. Plec<br>Steven G. Karr |

Although the preferred embodiment uses a digital receive beamformer, wherein the electrical signal corresponding to the returning echo from each active element, such as XDCR J of transducer array (FIG. 4A), is digitized simultaneously on each of the N channels by analog-to-digital converter 13 associated with each channel, this invention could equally be incorporated in other architectures. The architecture to support the embodiments of FIG. 1A, 1B-1, and 1B-2 would, however, need to support the ability to simultaneously acquire two receive beams per transmit beam. The essential requirement is that there exist means to acquire and store a coherent representation of the signals associated with each distinct receive beam, such as those designated 2a and 2b in FIG. 4A, preferably in digital form. Other beamformers, which employ analog rather than digital beamforming means to acquire multiple beams, may be modified by the addition of digitizers to capture the coherent output signals and thus made suitable for the invention disclosed here.

The transducer array 1 of FIG. 4A consists of a multiplicity of elements XDCR 1 to XDCR N that might be 128 or more in number.

The beamforming elements illustrated in FIG. 4A are shown for one channel. All other channels as indicated on FIG. 4A, are similar. The demultiplexer 3, multiplexer 4, summer 16 and central control blocks 18 and 19 are associated with all channels.

Each channel of the digital transmit beamformer is made up of transmit filter 5, digital modulator 6 and delay/filter 7. The transmit filter 5 is programmed to represent the complex envelope of the pulse to be transmitted. The digital modulator 6 up-converts the complex envelope to the transmit frequency and provides the appropriate phasing and apodization. The delay/filter 7 provides the bulk of the delay for focusing and filtering for suppression of spurious responses.

The transmitter for each channel is implemented with digital-to-analog converter (DAC) 8 and transmit amplifier 9. DAC 8 converts the digital samples of the transmit waveform to an analog signal. The transmit amplifier 9 sets the transmit power level and generates the high voltage pulses to drive the connected elements of the transducer array 1 for transmit beam formation. The pulse is routed to connected transducer elements through transmit demultiplexer 3. To support synthetic aperture scanning, each transmit amplifier 9 may be connected to one or more elements in the array.

The receiver for each channel is implemented by receive amplifier 12 which amplifies the signals from one element of the transducer array 1 and applies it to analog-to-digital converter (ADC) 13. The connection to the element of choice is effected by receive multiplexer 4, which can likewise select one or more elements for reception to support synthetic aperture scanning. ADC 13 converts each receive signal to a digital representation and the output is routed to the digital receive beamformer.

Each channel of the digital receive beamformer is implemented with filter/delay 14 and digital demodulator 15. Filter/delay 14 provides filtering for suppression of spurious responses and delay for focusing. The digital demodulator 15 provides phasing, apodization, and rotation to baseband. The capability of forming multiple receive beams is effected by filter/delay 14 and digital demodulator 15. These processing elements can be time-division multiplexed on a sample-by-sample basis to calculate two output signals (corresponding to signals on each of two receive beams) from one input signal. The two output signals are thus time-interleaved on a sample-by-sample basis, where each sample is an I and Q pair. It is understood that such time-division multiplexing can accomplish signal processing with for example two, three, four, etc., transmit beams associated with four, six, eight, etc., receive beams.

The rest of the signal processing to form receive beams is provided by digital summer 16 and receive filter 17. Summer 16 adds together similarly processed receive signals, similarly time-interleaved, from all the channels connected to other elements of the transducer array. Receive filter 17 is organized to process time-interleaved representations of the signals associated with each acquisition beam, and it provides programmable receive response shaping for these signals.

For the embodiment described, the output of receive filter 17 at 17a thus contains the coherent samples associated with spatially distinct receive beams, resulting from a single transmit excitation. The time-interleaved representation of the signals associated with pairs of acquisition beams is as follows:

$$I_{n,k} \quad (15)$$
$$Q_{n,k}$$
$$I_{n+1,k}$$
$$Q_{n+1,k}$$
$$I_{n,k+1}$$
$$Q_{n,k+1}$$
$$I_{n+1,k+1}$$
$$Q_{n+1,k+1}$$
$$\cdot$$
$$\cdot$$
$$\cdot$$

Here, the index n refers to distinct receive beam, and the index k refers to distinct ranges at which samples were taken.

The control functions for beam formation are schematically represented in the two central control blocks. In control block 18, an acquisition processor communicates with the rest of the system and provides high level control and downloading of frame parameters. A focusing processor computes the dynamic delay and apodization values required for transmit and receive beamformers and controls the digital receive beamformer to create two simultaneous receive beams.

Control block 19 schematically illustrates the front end control function. It sets the gain and bias levels for transmit and receive amplifiers 9 and 12. A frequency generator provides all of the necessary clocks including sampling clocks for ADCs 13 and DACs 8, and clocks for other digital circuits. Control block 19 also configures the front end multiplexer 4 for synthetic aperture scanning.

Figures 1, 4B:
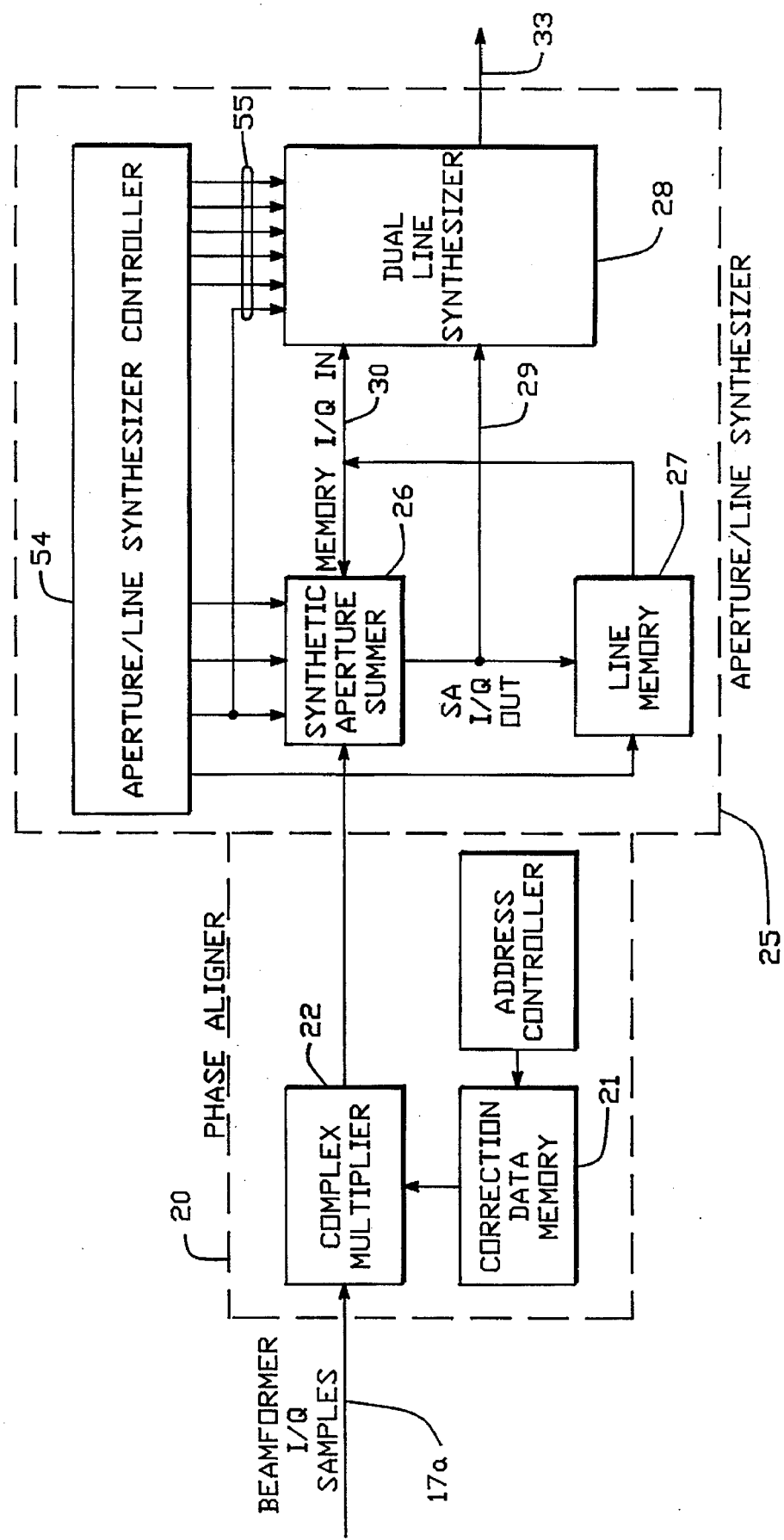
Figures 2, 4B:
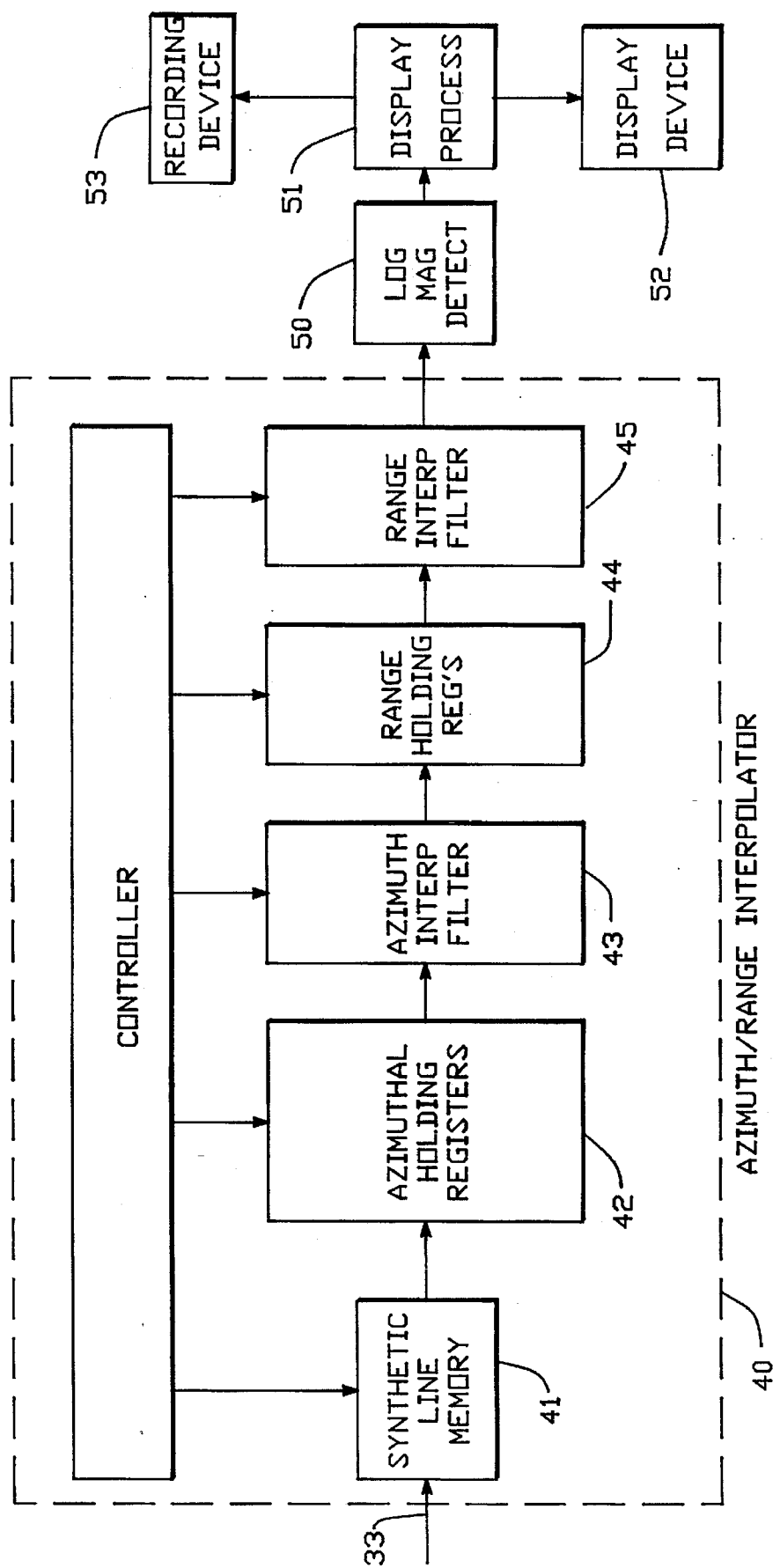

The line-dependent and range-dependent phase correction of the signal on line 17a is performed at phase aligner 20 shown in FIG. 4B-1. In one embodiment, the correction data is precalculated and stored in the correction data memory 21 of the phase aligner control 23. The correction data are read out of the correction data memory 21 in the same time-interleaved order as the data supplied by the digital receive beamformer, to apply corrections to data associated with distinct receive beams. The calculation performed by the complex multiplier 22 results in a phase rotation of each complex sample, where each sample is represented as a complex number in which I is the real part and Q is the imaginary part. For a phase correction of θ, the real part of the output of the phase aligner 20 is $I.\cos\theta - Q.\sin\theta$ the imaginary part is $Q.\cos\theta + I.\sin\theta$.

Figure 10:
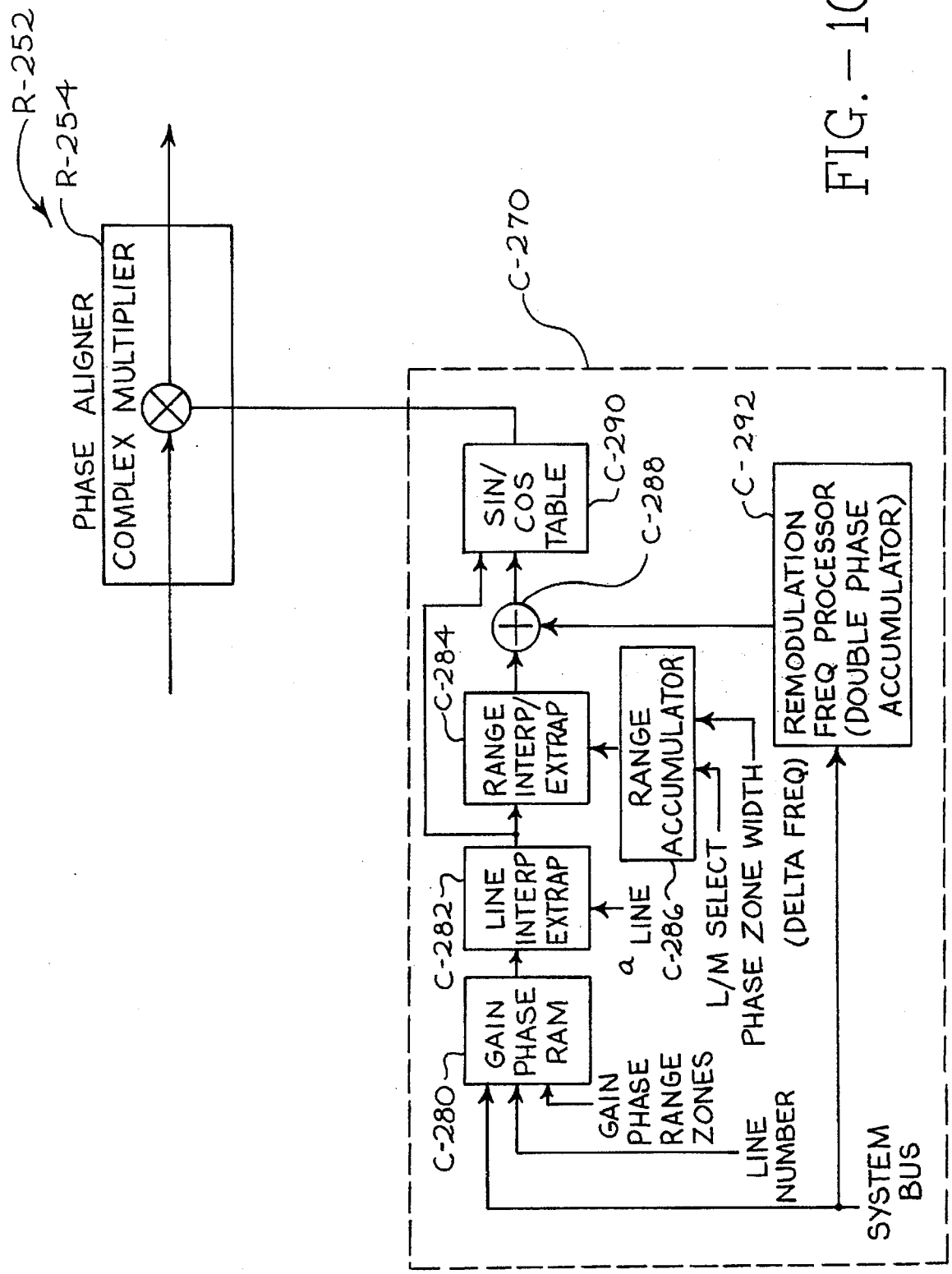
FIG. 10 depicts a block diagram schematic of a phase aligner.

A preferred embodiment of a phase aligner R-252 and its control within baseband processor control C-270 as depicted in FIG. 10 follows. As discussed herein and in the co-pending U.S. patent application entitled METHOD AND APPARATUS FOR RECEIVE BEAMFORMER SYSTEM, phase aligner R-252 and its control provide for (1) scan-line-dependent and range-dependent phase adjustments of the signal required to correct for phase differences resulting from line-to-line apodization changes, scan geometry, and non-aligned effective transmit and receive origins, (2) remodulation (frequency alignment) of the signal to correct for phase differences resulting from different transmit frequencies per scan line, and (3) gain adjustment per scan line. The advantage of the use of a scan-line-to-scan-line adjustable frequency mode on transmit and receive beamformation is the reduction of grating lobes (see co-pending application entitled: METHOD AND APPARATUS FOR ADJUSTABLE FREQUENCY SCANNING IN ULTRASOUND IMAGING, which discusses a scan-line-to-scan-line variable frequency mode).

The complex multiplier R-254 of phase aligner R-252 is substantially identical to complex multiplier 22 discussed above with respect to FIG. 4B-1.

The phase aligner includes a control function which is contained in a baseband processor control C-270 (FIG. 10). In this baseband processor control C-270, a scan-line-to-scan-line or beam-to-beam gain adjustment value and a phase adjustment value are generated in a time interleaved manner. As discussed above, the phase correction or adjustment value is the sum of the phase terms including: (1) a phase adjustment term required to correct for phase differences due to scan-line-to-scan-line apodization changes, and scan geometry which results in non-aligned effective transmit and receive origins (the scan-line-dependent and range-dependent phase adjustment term) and (2) a phase term required to remodulate the signal as though each line had used a common carrier frequency. As discussed herein and in co-pending U.S. patent application entitled: METHOD AND APPARATUS FOR TRANSMIT BEAMFORMER SYSTEM and METHOD AND APPARATUS FOR ADJUSTABLE FREQUENCY SCANNING IN ULTRASOUND IMAGING, using a frequency scaling factor or frequency vernier factor, each beam can have a different carrier frequency. The phase aligner accordingly provides for remodulation between beams so that all beams are adjusted for variation in carrier frequencies.

In operation a source data set including scan format geometry parameters, sparse scan line gain and delay value, interpolation coefficient and non-integer decimation factors are downloaded from the central control C-104 to the baseband processor control C-270. Additionally, frequency parameters used in the frequency profile generator of the central control C-104 are downloaded to the baseband processor control C-270.

The baseband processor control C-270 of FIG. 10 includes a gain and phase RAM C-280, a line interpolator C-282 which is supplied with pre-calculated and pre-stored line interpolation coefficients ($\alpha_{line}$) by the central control C-104, and a range interpolator C-284 with a range accumulator C-286, which is supplied with a rational decimation factor L/M and a phase zone width, both of which values are pre-calculated and pre-stored in the central control C-104.

Alternatively the range interpolator/extrapolator C-284 can be supplied with programmable interpolation/extrapolation coefficients which are, by way of example, either (1) pre-calculated and pre-stored in or calculated by the central control or (2) calculated locally in baseband processor control C-270 by a coefficient generator.

The baseband processor control C-270 also includes a remodulation frequency processor C-292 which is preferably implemented as a double phase accumulator. The double phase accumulator calculates phase adjustment values to correct for line-to-line frequency differences and thus to remodulate the signal as though a common carrier frequency had been used across all scan lines.

From the central control C-104, pre-calculated and pre-stored values representing the frequency differences between scan lines (delta frequency values) are sent to the remodulation frequency processor C-292. These frequency difference values are based on frequencies and frequency slopes. Accordingly, downloaded to baseband processor control C-270 from the central control for the two scan lines are the difference in frequencies between the scan lines and the difference in the rate of change of the frequency profiles over time. These values are calculated by the acquisition processor C-130 based on stored parameters and dependent upon the particular rational conversion factor L/M currently being used. The first accumulator of processor C-292 accumulates the difference in the rates of change of the frequency profiles over time between scan line while the second accumulator accumulates the difference in the frequencies between the scan lines over time. If there is no difference in the rate of change of the frequency profile over time, the first accumulator performs no function. With no difference in the rate changes of the frequencies between the scan lines, only the second accumulator accumulates the frequency differences over time resulting in a corrective remodulation phase value.

The phase adjustment due to scan-line-to-scan-line apodization changes, scan geometry which results in non-aligned transmit and receive origins, and the phase adjustment due to remodulating the signal to an effective common carrier frequency are added in a summer C-288 and the summed phase value is then converted in a look-up table C-290 to sine and cosine representations. As part of the look-up table C-290 function, the gain is multiplied by the sine and cosine representations. This value is applied to complex multiplier R-252.

It is to be understood that other embodiments of the baseband processor control are possible within the scope of this invention.

As indicated above the phase aligner R-252 ensures that coherent signal and sample relationships are maintained between scan lines. The transmit samples and the echo or receive samples of the signals from beams are defined as being coherent when sufficient information is stored, preserved, or maintained to enable the samples of the return signals to be phase and amplitude corrected from scan-line-to-scan-line. The process of actually making the phase and amplitude corrections need not have yet taken place, as long as sufficient information with respect to a reference is maintained.

When a signal sample is processed coherently, the processing continues to maintain sufficient information to perform phase and amplitude correction at a later time. When two or more samples are processed coherently (e.g., coherently summed), the phase and amplitude corrections necessary for phase and amplitude alignment must have previously been performed.

The output of the phase aligner, such as phase aligner 20 or R-252, is presented to the aperture/line synthesizer 25, still in a time-interleaved format containing the coherent data associated with two spatially distinct receive beams. When the system is not operating in a synthetic aperture mode, or when data are associated with the first of a plurality of transmit excitations for a synthetic aperture mode, the data are passed unchanged through the synthetic aperture summer 26 and stored in line memory 27. Incoming data associated with a plurality of transmit excitations for a synthetic aperture mode after the first transmit excitation are summed, sample by sample, with the corresponding data from line memory 27. These corresponding data are in a time-interleaved format containing the coherent data associated with the same two spatially distinct receive beams as the incoming data. The output of the synthetic aperture summer 26 is thus in a time-interleaved format containing the coherent data associated with the same two spatially distinct receive beams, accumulated over a plurality of transmit excitations.

The output of the synthetic aperture summer 26 is presented to the input of the dual-line synthesizer 28. When the system is not operating in a synthetic aperature mode, the dual line synthesizer 28 is enabled to process all the data at its input connected to the SA I/Q OUT bus 29. Otherwise, the dual line synthesizer 28 is enabled to process these data only when the output of the synthetic aperture summer 26 is associated with the summation following the last transmit excitation of a synthetic aperture excitation sequence.

The dual-line synthesizer 28 is controlled by controller 54 over lines 55 and performs two processing functions. First, it averages coherent samples of distinct receive beams in a pairwise fashion according to one or more of the preferred embodiments of the invention. Second, it filters the coherent samples in azimuth with a three-tap filter. These processing functions can be accomplished in any order and also in a combined and/or simultaneous manner.

The above two processing functions are performed, in a preferred embodiment, through the use of a four-tap filter equivalent to the convolution of the above two simpler filters. This four-tap filter is, for example, characterized by tap weights of [1, 3, 3, 1]. The processing in the dual line synthesizer 28 is organized in such a way that the coherent data at its output is in the same time-interleaved format as the output of the digital beamformer; however, the coherent data at the output 33 of the dual line synthesizer 28 are associated with two spatially distinct synthetic scan lines (each spatially distinct from receive or transmit scan lines) whereas the output 17a of the digital beamformer is associated with two spatially distinct receive scan lines.

Figure 5:
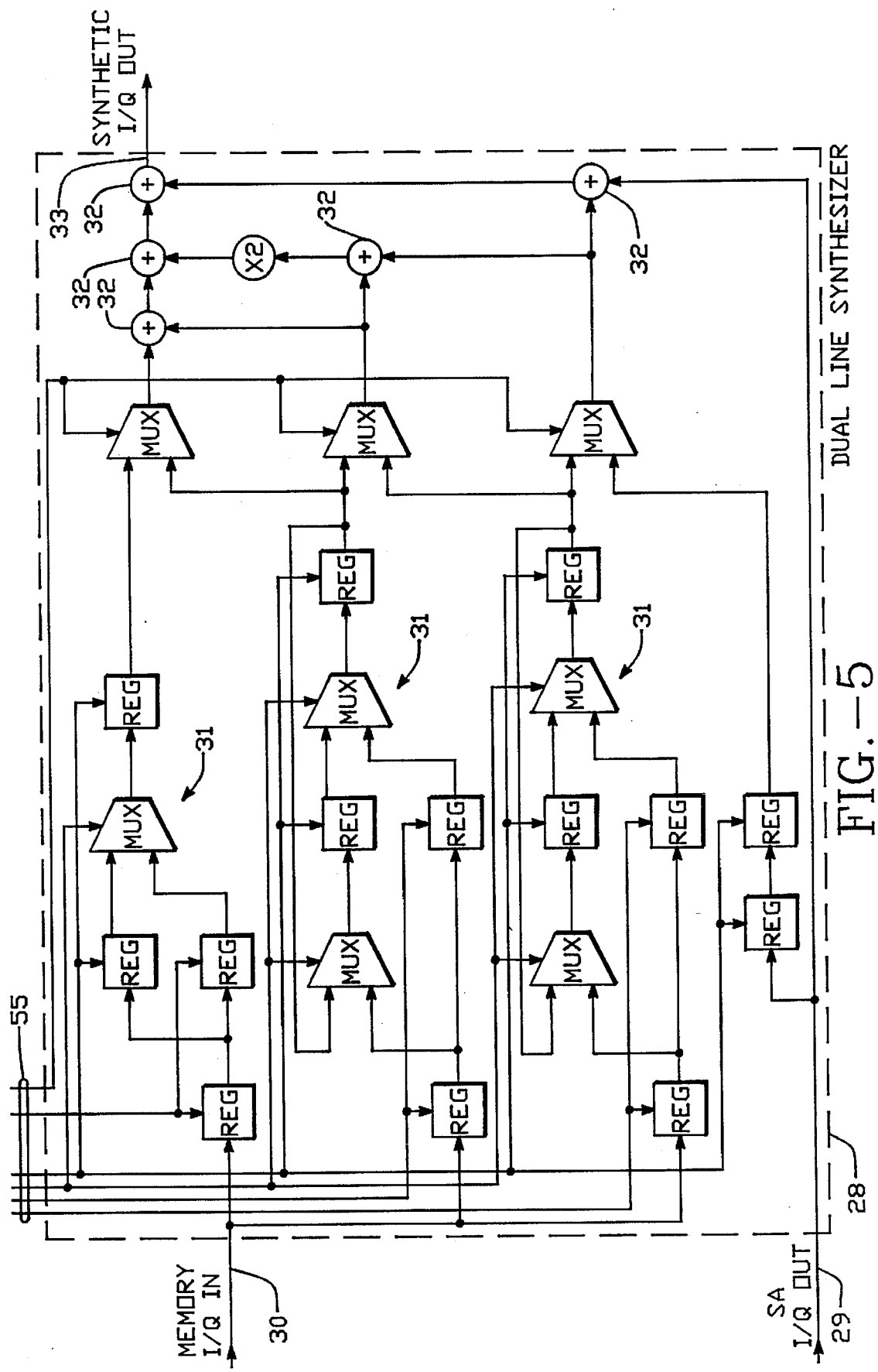
FIG. 5 is a schematic block diagram of a dual-line synthesizer apparatus which can effect the calculation of synthetic samples of both the first type and the second type of this invention.

The means to perform this function, in a particular embodiment, is shown in greater detail in FIG. 5. In this particular embodiment, in order to calculate the samples for two synthetic scan lines, the processing uses the corresponding samples from five receive scan lines. Two of these five are supplied from the synthetic aperture summer 26 at 29 and the remaining three are supplied from the line memory 27 at 30. The memory thus operates at a higher rate than the summing circuitry, as it must be able to store two lines and access three lines (or five lines when doing synthetic aperture scanning) for every two lines that are input to or output from the aperture/line synthesizer 25. Because of this rate differential, three input stages of the dual line synthesizer 28 have holding registers 31 to store the I and Q samples that appear on the MEMORY I/Q IN bus at 30. The adders 32 and a times 2 multiplier form an array to effect a four tap filter with tap weights of [1, 3, 3, 1]. The input data and control is organized to effect an output data sequence that can be represented as a sequence of inner products of this weight vector and a sequence of input data vectors represented as:

$$[I_{n-4} \quad I_{n-3} \quad I_{n-2} \quad I_{n-1}]_k \quad (16)$$
$$[Q_{n-4} \quad Q_{n-3} \quad Q_{n-2} \quad Q_{n-1}]_k$$
$$[I_{n-3} \quad I_{n-2} \quad I_{n-1} \quad I_n]_k$$
$$[Q_{n-3} \quad Q_{n-2} \quad Q_{n-1} \quad Q_n]_k$$
$$[I_{n-4} \quad I_{n-3} \quad I_{n-2} \quad I_{n-1}]_{k+1}$$
$$[Q_{n-4} \quad Q_{n-3} \quad Q_{n-2} \quad Q_{n-1}]_{k+1}$$
$$[I_{n-3} \quad I_{n-2} \quad I_{n-1} \quad I_n]_{k+1}$$
$$[Q_{n-3} \quad Q_{n-2} \quad Q_{n-1} \quad Q_n]_{k+1}$$
$$\vdots$$

As before, the index n refers to distinct receive scan lines, and the index k refers to distinct ranges at which samples were taken. These data are shifted right by three bit positions to effect a final divide-by-eight at the output 33 of the dual line synthesizer 28.

The output 33 of the aperture/line synthesizer 25 consists of synthetic lines of type one and two. A further step which can be a precedent, simultaneous or subsequent step in the method is the synthesis of additional coherent image samples (as these steps are predetection) through azimuthal interpolation (FIG. 4B-2) using by way of example only, any of the techniques previously described. In the preferred embodiment, the I and Q samples associated with each of four adjacent synthetic scan lines are used to interpolate one new synthetic scan line in the center of the four, also represented in I and Q form. One of two selectable filters is used in the preferred embodiment, the tap weights for one being [0.5 .5 0] and the other being [−0.064 0.564 0.564 −0.064]. This step doubles the azimuthal sample density of the coherent image in order to minimize distortions and artifacts due to subsequent non-linear detection for video image display.

Synthetic samples of the first and second types to be presented to the azimuth/range interpolator 40 are stored in synthetic line memory 41. The data are retrieved from synthetic line memory 41 and stored in azimuthal holding registers 42, the function of which is to re-order the data and to present it to the azimuth interpolation filter 43 in the following sequence:

$$[I_{n-3} \quad I_{n-2} \quad I_{n-1} \quad I_n]_k \quad (17)$$
$$[Q_{n-3} \quad Q_{n-2} \quad Q_{n-1} \quad Q_n]_k$$
$$[I_{n-3} \quad I_{n-2} \quad I_{n-1} \quad I_n]_{k+1}$$
$$[Q_{n-3} \quad Q_{n-2} \quad Q_{n-1} \quad Q_n]_{k+1}$$
$$[I_{n-3} \quad I_{n-2} \quad I_{n-1} \quad I_n]_{k+2}$$
$$[Q_{n-3} \quad Q_{n-2} \quad Q_{n-1} \quad Q_n]_{k+2}$$
$$[I_{n-3} \quad I_{n-2} \quad I_{n-1} \quad I_n]_{k+3}$$
$$[Q_{n-3} \quad Q_{n-2} \quad Q_{n-1} \quad Q_n]_{k+3}$$
$$\vdots$$

Here, the index n refers to distinct synthetic scan lines, and the index k refers to distinct ranges at which samples were taken. The azimuth interpolation filter of block 43 is a four tap filter, and its output contains samples of synthetic lines of the first and second types (when samples are passed through unchanged) and/or of the third type (when interpolation filtering is applied). The output of the azimuth interpolation filter of block 43 contains data for two synthetic scan lines at a time, organized as follows:

$$\begin{array}{l} I_{n-2,k} \\ Q_{n-2,k} \\ I_{n-1.5,k} \\ Q_{n-1.5,k} \\ I_{n-2,k+1} \\ Q_{n-2,k+1} \\ I_{n-1.5,k+1} \\ Q_{n-1.5,k+1} \\ \vdots \end{array} \quad (18)$$

Here, a fractional index n has been introduced to enumerate synthetic scan lines of the third type. As before, the index k refers to distinct ranges at which samples were taken.

Another further step in the preferred embodiment is the synthesis of additional coherent image samples on synthetic scan lines and/or transmit or receive scan lines through interpolation in range. In the preferred embodiment, each four adjacent samples on each synthetic scan line are used to interpolate one new coherent sample in the center of the four, also represented in I and Q form; the available interpolation filter tap weights are identical to those above. This step doubles the sample density of the coherent image again, this time in range.

The final step of range interpolation, prior to detection, is performed by range holding registers 44 and range interpolation filter of block 45. Range holding registers 44 re-order the incoming data and present it to the range interpolation filter block 45 as follows:

$$\begin{array}{llll} [I_{k-4} & I_{k-3} & I_{k-2} & I_{k-1}]_{n-2} \\ [Q_{k-4} & Q_{k-3} & Q_{k-2} & Q_{k-1}]_{n-2} \\ [I_{k-4} & I_{k-3} & I_{k-2} & I_{k-1}]_{n-1.5} \\ [Q_{k-4} & Q_{k-3} & Q_{k-2} & Q_{k-1}]_{n-1.5} \\ [I_{k-3} & I_{k-2} & I_{k-1} & I_{k}]_{n-2} \\ [Q_{k-3} & Q_{k-2} & Q_{k-1} & Q_{k}]_{n-2} \\ [I_{k-3} & I_{k-2} & I_{k-1} & I_{k}]_{n-1.5} \\ [Q_{k-3} & Q_{k-2} & Q_{k-1} & Q_{k}]_{n-1.5} \\ \vdots \end{array} \quad (19)$$

Range interpolation filter of block 45 is a four-tap filter identical in structure in a preferred embodiment to azimuth interpolation filter of block 43. The sequence of data samples at its output is similar to that at the output of the azimuth interpolation filter, except that it is more densely sampled in range, as follows:

$$\begin{array}{l} I_{n-2,k-3} \\ Q_{n-2,k-3} \\ I_{n-1.5,k-3} \\ Q_{n-1.5,k-3} \\ I_{n-2,k-2.5} \\ Q_{n-2,k-2.5} \\ I_{n-1.5,k-2.5} \\ Q_{n-1.5,k-2.5} \\ \vdots \end{array} \quad (20)$$

Following the above interpolation operation, the coherent I and Q baseband signals for all synthetic scan lines are then magnitude detected and log compressed at 50 prior to scan conversion at 51 and display at 52 and/or recording at 53, all of which is well-known to the prior art.

In the preferred embodiment, the aperture/line synthesizer can be bypassed for scan formats using only type three and/or four synthetic samples.

Figure 4C:
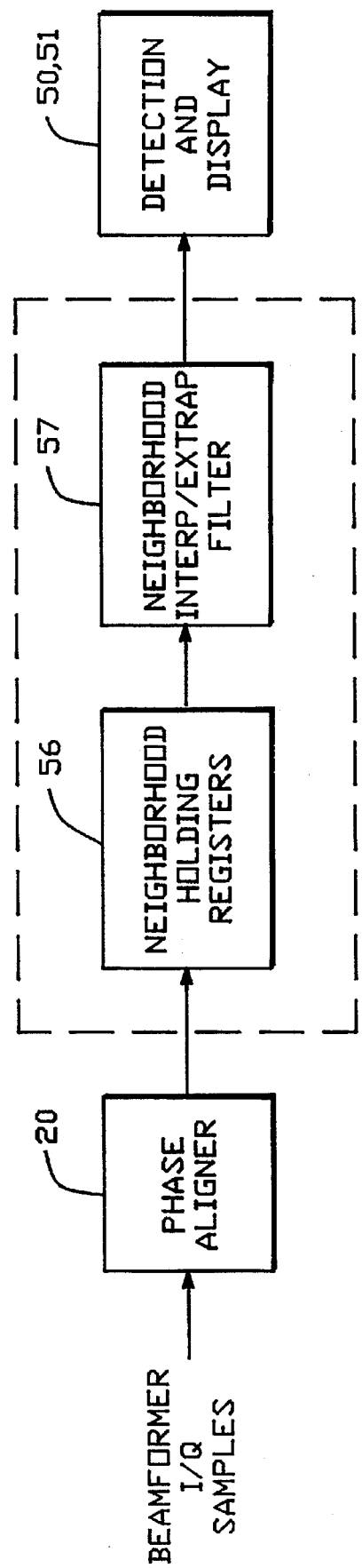
FIG. 4C is a schematic block diagram of an embodiment of an apparatus of the invention to effect synthetic samples on synthetic scan lines, using neighborhood interpolation and/or extrapolation techniques.

Alternatively as depicted in FIG. 4C neighborhood interpolation/extrapolation techniques can be used on two- and three-dimensional data fields in order to output denser two-dimensional and three-dimensional data fields. The input data for this operation is collected and stored in neighborhood holding register 56 and the neighborhood interpolation and/or extrapolation operations are carried out preferably using the filter of block 57. These neighborhood techniques are used to process coherent samples with varying ranges.

Such neighborhood techniques can be used by themselves as shown in FIG. 4C or alternatively can be used in combination with any of the preceding techniques for generating the first, second, third and/or fourth types of synthetic samples.

Further, in other embodiments, extrapolation techniques can be used alone or in combination with the interpolation techniques described above.

in still other embodiments, detection can be performed on acquired samples in addition to synthesized coherent samples.

VI. Compatibility with Other Formats Used in Ultrasonic Imaging:

The method and apparatus disclosed are generally compatible with most B-mode ultrasound imaging formats. Although dynamic focusing and dynamic apodization are not strictly required for use of this invention, they greatly enhance the value of the invention. The methods and apparatus disclosed, while shown for one dimensional transducer arrays, which are N×1, can be extended advantageously to two-dimensional arrays which are N×N or N×M elements.

Accordingly, the present invention can enhance the video image by increasing the frame rate by increasing the field of data samples through the creation of synthetic samples and by correction for geometric distortion. The sample field density is increased through linear and/or non-linear interpolation and/or extrapolation techniques.

All of the above embodiments have the advantage of increasing the density of samples in the field without increasing the number of transmit excitations for both two- and three-dimensional imaging.

Other aspects and objects of the invention can be obtained from a review of the claims and figures.

It is to be understood that other embodiments of the invention can be fabricated and come within the spirit and scope of the claims.

What is claimed is:

1. A method for imaging an object using coherent samples acquired on receive scan lines, which samples are representative of a signal from the object, the method comprising the steps of:
   (a) phase aligning the acquired coherent samples to effect beam-to-beam coherency; and
   (b) synthesizing at least one new sample from the phase-aligned samples.

2. The method of claim 1 wherein the synthesizing step comprises synthesizing at least two samples on a first synthetic scan line using coherent samples on receive scan lines at least two of which are associated with successive transmit events.

3. The method of claim 2 wherein said first synthetic scan line is colinear with a first receive scan line associated with a first transmit event and with a second receive scan line associated with a second transmit event.

4. The method of claim 2 wherein said first synthetic scan line is spatially distinct from said receive scan lines associated with successive transmit events.

5. The method of claims 3 or 4 further comprising synthesizing at least two samples on a second synthetic scan line using coherent samples on spatially distinct receive scan lines at least two of which receive scan lines are associated with the same transmit event.

6. The method of claim 5 further comprising synthesizing at least one further synthetic sample on a third synthetic scan line.

7. The method of claim 6 wherein the further synthetic sample is synthesized using at least one synthetic sample on said first synthetic scan line and at least one synthetic sample on said second synthetic scan line.

8. The method of claim 6 or 7 wherein the third synthetic scan line is spatially distinct from said first and second synthetic scan lines.

9. The method of claim 8 wherein the third synthetic scan line is spatially distinct from said transmit and receive scan lines.

10. The method of claim 6 or 7 wherein the third synthetic scan line is spatially distinct from said transmit and receive scan lines.

11. An apparatus for imaging an object using coherent samples acquired on receive scan lines, which samples are representative of a signal from the object, the apparatus comprising:
    (a) a phase aligner that adjusts the phase of the acquired coherent samples to effect beam-to-beam coherency; and
    (b) a synthesizer that uses the phase-aligned samples to synthesize at least one new sample.

12. The apparatus of claim 11 wherein the synthesizer synthesizes at least two samples on a first synthetic scan line using coherent samples on receive scan lines at least two of which are associated with successive transmit events.

13. The apparatus of claim 12 wherein said first synthetic scan line is colinear with a first receive scan line associated with a first transmit event and with a second receive scan line associated with a second transmit event.

14. The apparatus of claim 12 wherein said first synthetic scan line is spatially distinct from said receive scan lines associated with successive transmit events.

15. The apparatus of claims 13 or 14 wherein the synthesizer further synthesizes at least two samples on a second synthetic scan line using coherent samples on spatially distinct receive scan lines, at least two of which receive scan lines are associated with the same transmit event.

16. The apparatus of claim 15 wherein the synthesizer synthesizes at least one further synthetic sample on a third synthetic scan line.

17. The apparatus of claim 16 wherein the synthesizer synthesizes the further sample using at least one synthetic sample on said first synthetic scan line and at least one synthetic sample on said second synthetic scan line.

18. The apparatus of claim 17 wherein the third synthetic scan line is spatially distinct from said first and second synthetic scan lines.

19. The apparatus of claim 18 wherein the third synthetic scan line is spatially distinct from said transmit and receive scan lines.

20. The apparatus of claim 17 wherein the third synthetic scan line is spatially distinct from said transmit and receive scan lines.

21. The apparatus of claim 16 wherein the third synthetic scan line is spatially distinct from said first and second synthetic scan lines.

22. The apparatus of claim 21 wherein the third synthetic scan line is spatially distinct from said transmit and receive scan lines.

23. The apparatus of claim 17 wherein the third synthetic scan line is spatially distinct from said transmit and receive scan lines.

24. A method for ultrasonically imaging an object using a plurality of transmit excitation events to create transmit beams, sensing a signal from said object on one or more receive beams after each excitation event, and using acquired coherent samples of said signals, wherein each of said transmit beams is substantially aligned with a respective transmit scan line and each of said receive beams is substantially aligned with a respective receive scan line, said method comprising the steps of:
    (a) aligning the phase of said acquired coherent samples to effect beam-to-beam coherency; and
    (b) combining said phase-aligned acquired coherent samples to synthesize new coherent samples on synthetic scan lines each of which is spatially distinct from at least one of:
        (1) said receive scan lines; and
        (2) said transmit scan lines.

25. The method of claim 24 further comprising the step of detecting the synthesized coherent samples.

26. The method of claim 25 wherein both synthesized coherent samples and acquired coherent samples are detected.

27. The method of claim 24 wherein said step of combining comprises weighting and summing said phase-aligned coherent samples.

28. The method of claim 27 further comprising the step of selecting at least one weighting factor of unity, and using said weighting factor in the step of weighting and summing.

29. The method of claim 24 wherein each transmit excitation event results in one transmit beam for each of said plurality of transmit excitation events.

30. The method of claim 24 using acquired coherent samples associated with sequential pairs of transmit excitation events to create colinear transmit scan lines to effect a synthetic aperture scan throughout at least a portion of the field of view.

31. An apparatus for ultrasonically imaging an object using a plurality of transmit excitation events to create transmit beams, sensing a signal from said object on one or more receive beams after each excitation event, and using acquired coherent samples of said signals, wherein each of said transmit beams is substantially aligned with a respective transmit scan line and each of said receive beams is substantially aligned with a respective receive scan line, said apparatus comprising:

(a) a phase aligner that adjusts the phase of said acquired coherent samples to effect beam-to-beam coherency; and (b) a synthesizer that combines said phase-aligned acquired coherent samples to synthesize new coherent samples on synthetic scan lines each of which is spatially distinct from at least one of:
(1) said receive scan lines; and
(2) said transmit scan lines.

32. The apparatus of claim 31 further comprising a detector that detects the synthesized coherent samples.

33. The apparatus of claim 32 wherein the detector detects both synthesized coherent samples and acquired coherent samples.

34. The apparatus of claim 31 wherein said synthesizer combines said phase-aligned coherent samples by weighting and summing said phase-aligned coherent samples.

35. The apparatus of claim 31 wherein said synthesizer selects at least one weighting factor of unity, and uses said weighting factor in weighting and summing.

36. The apparatus of claim 31 wherein each transmit excitation event results in one transmit beam for each of said plurality of transmit excitation events.

37. The apparatus of claim 31 using acquired coherent samples associated with sequential pairs of transmit excitation events to create colinear transmit scan lines to effect a synthetic aperture scan throughout at least a portion of the field of view.

38. A method for ultrasonically imaging an object using a plurality of transmit excitation events to create transmit beams, sensing a signal from said object on a receive beam after each excitation event, and using acquired coherent samples of said signal, wherein each of said transmit beams is substantially aligned with a respective transmit scan line and said receive beam is substantially aligned with a respective receive scan line, and wherein said receive scan line is colinear with one of said transmit scan lines, said method comprising the steps of:

(a) aligning the phase of said acquired coherent samples associated with at least two of said plurality of transmit excitation events to effect beam-to-beam coherency; and (b) combining said phase-aligned coherent samples to synthesize new coherent samples on synthetic scan lines.

39. The method of claim 38 further comprising the step of detecting the synthesized coherent samples.

40. The method of claim 39 wherein both synthesized coherent samples and acquired coherent samples are detected.

41. The method of claim 38 wherein the step of combining comprises weighting and summing said phase-aligned coherent samples.

42. The method of claim 41 further comprising the step of selecting at least one weighting factor of unity, and using said weighting factor in the step of weighting and summing.

43. The method of claim 38 wherein each transmit excitation event results in one transmit beam for each of said plurality of transmit excitation events.

44. The method of claim 38 using acquired coherent samples associated with sequential pairs of transmit excitation events to create colinear transmit scan lines to effect a synthetic aperture scan throughout at least a portion of the field of view.

45. An apparatus for ultrasonically imaging an object using a plurality of transmit excitation events to create transmit beams, sensing a signal from said object on a receive beam after each excitation event, and using acquired coherent samples of said signal, wherein each of said transmit beams is substantially aligned with a respective transmit scan line and said receive beam is substantially aligned with a respective receive scan line, and wherein said receive scan line is colinear with one of said transmit scan lines, said apparatus comprising:

(a) a phase aligner that adjusts the phase of said acquired coherent samples associated with at least two of said plurality of transmit excitation events to effect beam-to-beam coherency; and (b) a synthesizer that combines said phase-aligned coherent samples to synthesize new coherent samples on synthetic scan lines.

46. The apparatus of claim 45 further comprising a detector that detects the synthesized coherent samples.

47. The apparatus of claim 46 wherein the detector detects both synthesized coherent samples and acquired coherent samples.

48. The apparatus of claim 45 wherein the synthesizer combines said phase-aligned coherent samples by weighting and summing said phase-aligned coherent samples.

49. The apparatus of claim 48 wherein said synthesizer selects at least one weighting factor of unity, and uses said weighting factor in the step of weighting and summing.

50. The apparatus of claim 45 wherein each transmit excitation event results in one transmit beam for each of said plurality of transmit excitation events.

51. The apparatus of claim 45 using acquired coherent samples associated with sequential pairs of transmit excitation events to create colinear transmit scan lines to effect a synthetic aperture scan throughout at least a portion of the field of view.

52. A method for ultrasonically imaging an object using a plurality of transmit excitation events to create transmit beams, sensing a signal from said object on each of a plurality of receive beams after each excitation event, and using acquired coherent samples of said signals, wherein each of said transmit beams is substantially aligned with a respective transmit scan line and each of said receive beams is substantially aligned with a respective receive scan liner and wherein each of said receive scan lines is spatially distinct from said transmit scan lines, said method comprising the steps of:

(a) aligning the phase of said acquired coherent samples to effect beam-to-beam coherency; and (b) combining said phase-aligned coherent samples to synthesize new coherent samples on synthetic scan lines each of which is spatially distinct from at least one of:
(1) said receive scan lines; and
(2) said transmit scan lines.

53. The method of claim 52 further comprising the step of detecting the synthesized coherent samples.

54. The method of claim 53 wherein both synthesized coherent samples and acquired coherent samples are detected.

55. The method of claim 52 wherein said step of combining comprises weighting and summing said phase-aligned coherent samples.

56. The method of claim 55 further comprising the step of selecting at least one weighting factor of unity, and using said weighting factor in the step of weighting and summing.

57. The method of claim 52 wherein each transmit excitation event results in one transmit beam for each of said plurality of transmit excitation events.

58. The method of claim 52 using acquired coherent samples associated with sequential pairs of transmit excitation events to create colinear transmit scan lines to effect a synthetic aperture scan throughout at least a portion of the field of view.

59. An apparatus for ultrasonically imaging an object using a plurality of transmit excitation events to create transmit beams, sensing a signal from said object on each of a plurality of receive beams after each excitation event, and using acquired coherent samples of said signals, wherein each of said transmit beams is substantially aligned with a respective transmit scan line and each of said receive beams is substantially aligned with a respective receive scan line, and wherein each of said receive scan lines is spatially distinct from said transmit scan lines, said apparatus comprising:

(a) a phase aligner that adjusts the phase of said coherent samples to effect beam-to-beam coherency; and (b) a synthesizer that combines said phase-aligned coherent samples to synthesize new coherent samples on synthetic scan lines each of which is spatially distinct from at least one of:

(1) said receive scan lines; and (2) said transmit scan lines.

60. The apparatus of claim 59 further comprising a detector that detects the synthesized coherent samples.

61. The apparatus of claim 60 wherein both synthesized coherent samples and acquired coherent samples are detected.

62. The apparatus of claim 59 wherein said synthesizer combines said phase-aligned coherent samples by weighting and summing said phase-aligned coherent samples.

63. The apparatus of claim 60 wherein said synthesizer selects at least one weighting factor of unity, and uses said weighting factor in weighting and summing.

64. The apparatus of claim 59 wherein each transmit excitation event results in one transmit beam for each of said plurality of transmit excitation events.

65. The apparatus of claim 59 using acquired coherent samples associated with sequential pairs of transmit excitation events to create colinear transmit scan lines to effect a synthetic aperture scan throughout at least a portion of the field of view.

66. A method for ultrasonically imaging an object using transmit beams associated with a plurality of transmit excitation events comprising the steps of:

(a) synthesizing at least two coherent samples on a first synthetic scan line using coherent samples on receive scan lines, at least two of which receive scan lines are associated with the same transmit event; and (b) detecting said synthesized samples.

67. The method of claim 66 wherein said first synthetic scan line is substantially colinear with a transmit scan line.

68. The method of claims 66 or 67 further comprising synthesizing at least two samples on a second synthetic scan line using coherent samples on receive scan lines associated with successive transmit excitation events.

69. The method of claim 68 wherein said second synthetic scan line is colinear with a first receive scan line associated with a first transmit event and with a second receive scan line associated with a second transmit event.

70. The method of claim 68 wherein said second synthetic scan line is spatially distinct from said receive scan lines associated with successive transmit events.

71. The method of claims 69 or 70 further comprising synthesizing at least one further synthetic sample on a third synthetic scan line.

72. The method of claim 71 wherein the further synthetic sample is synthesized using at least one synthetic sample on said first synthetic scan line and at least one synthetic sample on said second synthetic scan line.

73. The method of claim 72 wherein the third synthetic scan line is spatially distinct from said first and second synthetic scan lines.

74. The method of claim 73 wherein the third synthetic scan line ms spatially distinct from said transmit and receive scan lines.

75. The method of claim 72 wherein the third synthetic scan line ms spatially distinct from said transmit and receive scan lines.

76. The method of claim 71 wherein the third synthetic scan line ms spatially distinct from said first and second synthetic scan lines.

77. The method of claim 76 wherein the third synthetic scan line ms spatially distinct from said transmit and receive scan lines.

78. The method of claim 71 wherein the third synthetic scan line ms spatially distinct from said transmit and receive scan lines.

79. An apparatus for ultrasonically imaging an object using transmit beams associated with a plurality of transmit excitation events, comprising:

(a) a synthesizer that synthesizes at least two coherent samples on a first synthetic scan line using coherent samples on spatially distinct receive scan lines, at least two of which receive scan lines are associated with the same transmit event; and (b) a detector that detects said synthesized coherent samples.

80. The apparatus of claim 79 wherein said first synthetic scan line is substantially colinear with a transmit scan line.

81. The apparatus of claims 79 or 80 wherein said synthesizer synthesizes at least two samples on a second synthetic scan line using coherent samples on receive scan lines associated with successive transmit excitation events.

82. The apparatus of claim 81 wherein said second synthetic scan line is colinear with a first receive scan line associated with a first transmit event and with a second receive scan line associated with a second transmit event.

83. The apparatus of claim 82 wherein said synthesizer synthesizes at least one further synthetic sample on a third synthetic scan line.

84. The apparatus of claim 83 wherein said synthesizer synthesizes the further synthetic sample using at least one synthetic sample on said first synthetic scan line and at least one synthetic sample on said second synthetic scan line.

85. The apparatus of claim 84 wherein the third synthetic scan line ms spatially distinct from said first and second synthetic scan lines.

86. The apparatus of claim 85 wherein the third synthetic scan line ms spatially distinct from said transmit and receive scan lines.

87. The apparatus of claim 84 wherein the third synthetic scan line is spatially distinct from said transmit and receive scan lines.

88. The apparatus of claim 83 wherein the third synthetic scan line is spatially distinct from said first and second synthetic scan lines.

89. The apparatus of claim 88 wherein the third synthetic scan line is spatially distinct from said transmit and receive scan lines.

90. The apparatus of claim 83 wherein the third synthetic scan line is spatially distinct from said transmit and receive scan lines.

91. The apparatus of claim 81 wherein said second synthetic scan line is spatially distinct from said receive scan lines associated with successive transmit events.

92. The apparatus of claim 91 wherein said synthesizer synthesizes at least one further synthetic sample on a third synthetic scan line.

93. The apparatus of claim 92 wherein said synthesizer synthesizes the further synthetic sample using at least one synthetic sample on said first synthetic scan line and at least one synthetic sample on said second synthetic scan line.

94. The apparatus of claim 93 wherein the third synthetic scan line ms spatially distinct from said first and second synthetic scan lines.

95. The apparatus of claim 94 wherein the third synthetic scan line ms spatially distinct from said transmit and receive scan lines.

96. The apparatus of claim 93 wherein the third synthetic scan line is spatially distinct from said transmit and receive scan lines.

97. The apparatus of claim 92 wherein the third synthetic scan line ms spatially distinct from said first and second synthetic scan lines.

98. The apparatus of claim 97 wherein the third synthetic scan line is spatially distinct from said transmit and receive scan lines.

99. The apparatus of claim 92 wherein the third synthetic scan line ms spatially distinct from said transmit and receive scan lines.

100. A method for ultrasonically imaging an object using a plurality of transmit excitation events to create transmit beams, sensing a signal from said object on one or more of a plurality of receive beams after each excitation event, and using acquired coherent samples of said signal, wherein each of said transmit beams is substantially aligned with a respective transmit scan line and each of said receive beams is substantially aligned with a respective receive scan line, said method comprising the steps of:
  (a) synthesizing a plurality of coherent samples on synthetic scan lines using coherent samples on at least two spatially distinct receive scan lines; and
  (b) using at least one of said synthesized coherent samples to synthesize at least one further coherent sample.

101. The method of claim 100 wherein said further coherent sample is on a further synthetic scan line.

102. The method of claim 100 wherein said further coherent sample is on one of said synthetic scan lines.

103. The method of claim 100, 101 or 102 wherein the synthesizing step comprises using coherent samples on at least two spatially distinct receive scan lines associated with a single transmit event.

104. The method of claim 100, 101 or 102 wherein the synthesizing step comprises using coherent samples associated with at least two distinct transmit excitation events.

105. The method of claim 101 wherein a first and a second set of coherent samples; are respectively synthesized from:
  (a) acquired coherent samples on spatially distinct receive scan lines associated with a single transmit excitation event; and
  (b) acquired coherent samples on receive scan lines associated with distinct transmit excitation events.

106. The method of claim 105 wherein said first set of coherent samples is synthesized on a synthetic scan line colinear with a transmit scan line and said second set of coherent samples is synthesized on a synthetic scan line colinear with a receive scan line.

107. The method of claim 105 wherein said first set of coherent samples is synthesized on a synthetic scan line colinear with a transmit scan line and said second set of synthetic samples is synthesized on a synthetic scan line spatially distinct from a receive scan line.

108. The method of claim 101, 105, 106 or 107 wherein said further synthetic scan line is not colinear with said transmit or receive scan lines.

109. An apparatus for ultrasonically imaging an object using a plurality of transmit excitation events to create transmit beams, sensing a signal from said object on one or more of a plurality of receive beams after each excitation event, and using acquired coherent samples of said signal, wherein each of said transmit beams is substantially aligned with a respective transmit scan line and each of said receive beams is substantially aligned with a respective receive scan line, said apparatus comprising:
  (a) a synthesizer that synthesizes synthetic samples, said synthesizer:
    (1) using coherent samples on at least two spatially distinct receive scan lines to synthesize a plurality of coherent samples on synthetic scan lines; and
    (2) using at least one of said synthesized coherent samples to synthesize at least one further coherent sample; and
  (b) a detector that detects the synthesized coherent samples.

110. The apparatus of claim 109 wherein said further coherent sample is on a further synthetic scan line.

111. The apparatus of claim 110 wherein a first and a second set of coherent samples are respectively synthesized from:
  (a) acquired coherent samples on spatially distinct receive scan lines associated with a single transmit excitation event; and
  (b) acquired coherent samples on receive scan lines associated with distinct transmit excitation events.

112. The apparatus of claim 111 wherein said first set of coherent samples is synthesized on a synthetic scan line colinear with a transmit scan line and said second set of coherent samples is synthesized on a synthetic scan line colinear with a receive scan line.

113. The apparatus of claim 111 wherein said first set of coherent samples is synthesized on a synthetic scan line colinear with a transmit scan line and said second set of coherent samples is synthesized on a synthetic scan line spatially distinct from a receive scan line.

114. The apparatus of claim 110, 111, 112 or 113 wherein said further synthetic scan line is not colinear with said transmit or receive scan lines.

115. The apparatus of claim 109 wherein said further coherent sample is on one of said synthetic scan lines.

116. The apparatus of claim 109, 110 or 115 wherein said synthesizer uses coherent samples on at least two spatially distinct receive scan lines associated with a single transmit excitation event.

117. The apparatus of claim 109, 110 or 115 wherein said synthesizer uses coherent samples associated with at least two distinct transmit excitation events.

118. A method for ultrasonically imaging an object using transmit beams generated from a plurality of transmit excitation events and using coherent samples acquired on at least two spatially distinct receive scan lines associated with the same transmit excitation event, which samples are representative of a signal from an object, said method comprising the steps of:
  (a) synthesizing a plurality of coherent samples on synthetic scan lines using said coherent samples, where the number of synthetic scan lines is greater than the number of receive scan lines over at least a portion of the field of view; and (b) detecting said synthesized coherent samples.

119. An apparatus for creating an ultrasonic image of an object using transmit beams generated from a plurality of transmit excitation events and using coherent samples acquired on at least two spatially distinct receive scan lines associated with the same transmit excitation event, which samples are representative of a signal from an object, comprising:

(a) a synthesizer that uses said coherent samples to synthesize a plurality of coherent samples on synthetic scan lines, where the number of synthetic scan lines is greater than the number of receive scan lines over at least a portion of the field of view; and (b) a detector that detects said synthesized samples.

120. A method for creating an ultrasonic image of an object using a plurality of transmit excitation events to create transmit beams, sensing a signal from said object after each excitation event on a plurality of receive beams and using acquired samples of said signals, wherein each of said transmit beams is substantially aligned with a respective transmit scan line and each of said receive beams is substantially aligned with a respective receive scan line, and wherein each of said receive scan lines is spatially distinct said transmit scan lines, said method comprising the steps of:

(a) combining said acquired coherent samples to synthesize new coherent samples on synthetic scan lines which are spatially distinct from said receive scan lines; and (b) detecting said synthesized coherent samples.

121. An apparatus for creating an ultrasonic image of an object using a plurality of transmit excitation events to create transmit beams, sensing a signal from said object after each excitation event on a plurality of receive beams and using acquired samples of said signals, wherein each of said transmit beams is substantially aligned with a respective transmit scan line and each of said receive beams is substantially aligned with a respective receive scan line, and wherein each of said receive scan lines is spatially distinct from said transmit scan lines, said apparatus comprising:

(a) a synthesizer that combines said acquired coherent samples to synthesize new coherent samples on synthetic scan lines which are spatially distinct from said receive scan lines; and (b) a detector which detects said synthesized samples.

122. An apparatus for ultrasonically imaging an object using coherent samples acquired on receive scan lines, which samples are representative of a signal from the object, the apparatus comprising:

(a) a control providing phase adjustment data; and (b) a phase adjuster connected to receive said coherent samples, the phase adjuster using the phase adjustment data to operate on the samples to effect phase coherence between samples.

123. The apparatus of claim 122 wherein:

the phase adjuster adjusts the phase of at least one of: (1) coherent samples on a first receive scan line relative to coherent samples on a second receive scan line; and (2) coherent samples relative to other coherent samples on the same receive same scan line.

124. The apparatus of claim 122 wherein:

said phase adjuster operates on acquired coherent samples to effect phase coherence between samples on different scan lines.

125. The apparatus of claim 122 wherein:

said phase adjuster operates on acquired coherent samples to effect phase coherence between samples on the same scan line.

126. The apparatus of claim 122 wherein:

said phase adjuster operates on acquired coherent samples to effect beam-to-beam coherency in at least one of azimuth, elevation, and range.

127. The apparatus of claim 122 wherein:

said phase adjuster remodulates acquired coherent samples on a receive scan line.

128. The apparatus of claim 127 wherein said phase adjuster remodulates acquired coherent samples associated with distinct beams using different frequencies to effect beam-to-beam coherence.

129. The apparatus of claim 122 wherein the phase adjuster comprises a phase rotator.

130. The apparatus of claim 122 wherein the phase adjuster comprises a complex value multiplier.

131. An method for ultrasonically imaging an object using coherent samples acquired on receive scan lines, which samples are representative of a signal from the object, the method comprising:

(a) providing phase adjustment data; and (b) adjusting the phase of said samples by using the phase adjustment data to operate on the samples to effect phase coherence between samples.

132. The method of claim 131 comprising:

adjusting the phase of at least one of: (1) coherent samples formed on a first receive scan line relative to coherent samples on a second receive scan line; and (2) coherent samples relative to other coherent samples on the same receive same scan line.

133. The method of claim 131 comprising:

operating on the acquired coherent samples to effect phase coherence between samples on different scan lines.

134. The method of claim 131 comprising:

operating on acquired coherent samples to effect phase coherence between samples on the same scan line.

135. The method of claim 131 comprising:

operating on acquired coherent samples to effect beam-to-beam coherency in at least one of azimuth, elevation, and range.

136. The method of claim 131 comprising:

remodulating acquired coherent samples on a receive scan line.

137. The method of claim 136 wherein the step of remodulating comprises remodulating acquired coherent samples associated with distinct beams using different frequencies to effect beam-to-beam coherence.

138. The method of claim 131 wherein the step of adjusting comprises using a phase rotator.

139. The method of claim 131 wherein the step of adjusting comprises using a complex value multiplier.

* * * * *

UNITED STATES PATENT AND TRADEMARK OFFICE
CERTIFICATE OF CORRECTION

PATENT NO. : 5,623,928
DATED : April 29, 1997
INVENTOR(S) : J. Nelson Wright et al.

It is certified that error appears in the above-indentified patent and that said Letters Patent is hereby corrected as shown below:

In column 1, "UNDER CROSS REFERENCE TO RELATED APPLICATIONS", at the end of the list of patents please add the following:

| | | |
|---|---|---|
| METHOD AND APPARATUS FOR ADJUSTABLE FREQUENCY SCANNING IN ULTRASOUND IMAGING | J. Nelson Wright<br>Christopher R. Cole<br>Albert Gee<br>Hugh G. Larsen<br>Samuel H. Maslak | ACUS-1022<br>SRM/WSW |

In column 5, line 59, replace "15B" with --6B--.

In column 8, line 61, replace "$\omega_d=2f_d=a$" with --$\omega_d=2\pi f_d=a$--.

In column 9, line 7, replace "my" with --may--.

In column 10, line 42, replace the first occurrence of "$I_1$," with --$I_0$--.

In column 10, line 50, replace "beans" with --beams--.

UNITED STATES PATENT AND TRADEMARK OFFICE
CERTIFICATE OF CORRECTION

PATENT NO. : 5,623,928
DATED : April 29, 1997
INVENTOR(S) : J. Nelson Wright et al.

It is certified that error appears in the above-identified patent and that said Letters Patent is hereby corrected as shown below:

In column 10, line 51, replace "$_{R01}$," with --$R_{01}$,--.

In column 14, lines 39 and 40, replace "coordination" with --combination--.

In column 16, line 48, after "for" insert --More--.

In the Claims

In Claim 52, line 8, replace "liner" with --line--.

In Claim 63, line 1, replace "60" with --62--.

In Claim 74, line 2, replace "ms" with --is--.

In Claim 75, line 2, replace "ms" with --is--.

In Claim 76, line 2, replace "ms" with --is--.

In Claim 77, line 2, replace "ms" with --is--.

In Claim 78, line 2, replace "ms" with --is--.

In Claim 85, line 2, replace "ms" with --is--.

In Claim 86, line 2, replace "ms" with --is--.

UNITED STATES PATENT AND TRADEMARK OFFICE
CERTIFICATE OF CORRECTION

PATENT NO. : 5,623,928
DATED : April 29, 1997
INVENTOR(S) : J. Nelson Wright et al.   Page 3 of 3

It is certified that error appears in the above-identified patent and that said Letters Patent is hereby corrected as shown below:

<u>In the Claims (cont'd)</u>

In Claim 94, line 2, replace "ms" with --is--.

In Claim 95, line 2, replace "ms" with --is--.

In Claim 97, line 2, replace "ms" with --is--.

In Claim 99, line 2, replace "ms" with --is--.

In Claim 105, line 2, delete ";" immediately after "samples".

In Claim 120, line 10, before "said" insert --from--.

In Claim 123, line 6, delete "same".

In Claim 132, line 6, delete "same".

Signed and Sealed this

Eighteenth Day of August, 1998

Attest:

BRUCE LEHMAN

*Attesting Officer*  *Commissioner of Patents and Trademarks*